US006605434B1

(12) United States Patent
Ferrie et al.

(10) Patent No.: US 6,605,434 B1
(45) Date of Patent: Aug. 12, 2003

(54) DIRECT BACTERIAL LYSATE SEQUENCING

(75) Inventors: Andrew Ferrie, Tewksbury, MA (US); Haibing Zhong, Annandale, VA (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 09/526,731

(22) Filed: Mar. 16, 2000

Related U.S. Application Data

(60) Provisional application No. 60/124,676, filed on Mar. 16, 1999.
(51) Int. Cl.[7] .......................... C12Q 1/68; C12P 19/34; G01N 33/53; G01N 15/06; C07H 21/00
(52) U.S. Cl. ........................ 435/6; 435/91.1; 435/91.2; 435/810; 435/968; 204/461; 422/68.1; 536/25.32
(58) Field of Search .......................... 435/6, 91.1, 91.2, 435/810, 968; 536/25.32; 422/68.1; 204/461

(56) References Cited

U.S. PATENT DOCUMENTS

| | | | |
|---|---|---|---|
| 4,757,141 A | 7/1988 | Fung et al. | 536/27 |
| 5,141,813 A | 8/1992 | Nelson | 428/402 |
| 5,151,507 A | 9/1992 | Hobbs, Jr. et al. | 536/23 |
| 5,185,242 A | 2/1993 | Keating et al. | 435/6 |
| 5,231,191 A | 7/1993 | Woo et al. | 549/220 |
| 5,332,666 A | 7/1994 | Prober et al. | 435/91.5 |
| 5,366,860 A | * 11/1994 | Bergot | 435/6 |
| 5,401,837 A | 3/1995 | Nelson | 536/25.32 |
| 5,432,065 A | 7/1995 | Fuller | 435/91.1 |
| 5,723,298 A | 3/1998 | Oommen et al. | 435/6 |
| 5,756,285 A | 5/1998 | Fuller | 435/6 |
| 5,766,852 A | 6/1998 | Down et al. | 435/6 |
| 5,798,210 A | 8/1998 | Canard et al. | 435/6 |
| 5,800,995 A | * 9/1998 | Patonay et al. | 435/6 |
| 5,817,797 A | 10/1998 | Mitchell et al. | 536/25.3 |
| 5,821,058 A | 10/1998 | Smith et al. | 435/6 |
| 5,831,065 A | 11/1998 | Brenner et al. | 536/24.3 |
| 5,837,529 A | 11/1998 | Wan et al. | 435/259 |
| 5,847,162 A | 12/1998 | Lee et al. | 549/227 |
| 5,849,542 A | 12/1998 | Reeve et al. | 435/91.1 |
| 5,851,765 A | 12/1998 | Köster | 435/6 |
| 5,876,936 A | 3/1999 | Ju | 435/6 |
| 6,225,092 B1 | * 5/2001 | Kilger et al. | 435/91.2 |

FOREIGN PATENT DOCUMENTS

| | | |
|---|---|---|
| EP | 0 753 584 A1 | 1/1997 |
| WO | WO 97/13810 | 4/1997 |
| WO | WO 97/20949 | 6/1997 |
| WO | WO 97/36960 | 10/1997 |
| WO | WO 97/40104 | 10/1997 |
| WO | WO 97/49769 | 12/1997 |
| WO | WO 98/14612 | 4/1998 |
| WO | WO 98/21361 | 5/1998 |

OTHER PUBLICATIONS

Maniatis et al. Molecular Cloning: A Laboratory Manual. Cold Spring Harbor Laboratory, 1982. pp. 88–89.*
O'Brien, S. et al., Direct Cycle Sequencing of Bacterial Lysates Using applied Biosystems Automated DNA Sequencer; Methods in Molecular and Cellular Biology vol. 5, pp. 363–366 (1995).*
Kristensen et al. DNA Sequence. 1991. vol. 1, No. 4, pp. 227–232.*
Bergstrom, D. et al., "Palladium–Mediated Coupling between Organic Disulfides and Nucleic Acid Constituents," *J. Am. Chem. Soc.* 111:375–375 (1989).
Chen, Q. et al., "Automated DNA Sequencing Requiring No DNA Template Purification," *BioTechniques* 21:453–457 (1996).
Chu, B.C.F. et al., "Derivatization of unprotected polynucleotides," *Nucl. Acid. Res.* 11:6513–6529 (1983).
Fleischmann, R.D. et al., "Whole–Genome Random Sequencing and Assembly of *Haemophilus influenzae* Rd," *Science* 269:496–512 (1995).
Fraser, C.M. et al., "The Minimal Gene Complement of *Mycoplasma genitialium*," *Science* 270:397–403 (1995).
Gebeyehu, G. et al., "Novel biotinylated nucleotide—analogs for labeling and colorimetric detection of DNA," *Nucl. Acids. Res.* 15:4513–4534 (1987).
Gibson, K.J. et al., "Synthesis and application of derivatizable oligonucleotides," *Nucl. Acids Res.* 15:6455–6467 (1987).
Haralambidis, J. et al., "Preparation of base–modified nucleosides suitable for non–radioactive label attachment and their incorporation into synthetic oligodeoxyribonucleotides," *Nucl. Acids Res.* 15:4857–4876 (1987).
Heiner, C.R. et al., "Sequencing Multimegabase–Template DNA with BigDye Terminator Chemistry," *Genome Res.* 8:557–561 (May 1998).
Himmelreich, R. et al., "Complete sequence analysis of the genome of the bacterium *Mycoplasma pneumoniae*," *Nucl. Acids Res.* 24:4420–4449 (1996).
Hobbs, Jr., F.W., "Palladium–Catalyzed Synthesis of Alkynylamino Nucleosides. A Universal Linker for Nucleic Acids," *J. Org. Chem.* 54:3420–3422 (1989).
Hultner, M.L. and Cleaver, J.E., "A Bacterial Plasmid DNA Miniprep Using Microwave Lysis," *Biotechniques* 16:990–994 (1994).

(List continued on next page.)

*Primary Examiner*—W. Gary Jones
*Assistant Examiner*—Arun Kr. Chakrabarti
(74) *Attorney, Agent, or Firm*—Human Genome Sciences, Inc.

(57) ABSTRACT

The present invention relates to novel methods for sequencing nucleic acid molecules. More specifically, methods are provided for sequencing nucleic acid molecules present in bacterial lysates without the need to purify nucleic acid templates from highly soluble cellular components.

32 Claims, 14 Drawing Sheets

OTHER PUBLICATIONS

Hung, S. et al., "Energy Transfer Primers with 5–or 6–Carboxyrhodamine–6G as Acceptor–Chromophores," *Anal. Biochem.* 238:165–170 (1996).

Hung, S. et al., "Cyanine Dyes with High Absorption Cross Section as Donor Chromophores in Energy Transfer Primers," *Anal. Biochem.* 243:15–27 (1996).

Hung, S. et al., "Optimization of Spectroscopic and Electrophoretic Properties of Energy Transfer Primers," *Anal. Biochem.* 252:78–88 (Oct. 1997).

Hung, S. et al., "Comparison of Fluorescence Energy Transfer Primers with Different Donor–Acceptor Dye Combinations," *Anal. Biochem.* 255:32–38 (Jan. 1998).

Iannelli, F. et al., "Direct Sequencing of Long Polymerase Chain Reaction Fragments," *Mol. Biotechnol.* 10:183–185 (Oct. 1998).

Ju, J. et al., "Fluorescence energy transfer dye–labeled primers for DNA sequencing and analysis," *Proc. Natl. Acad. Sci. USA* 92:4347–4351 (1995).

Lee, L.G. et al., "Allelic discrimination by nick–translation PCR with fluorogenic probes," *Nucl. Acids Res.* 21:3761–3766 (1993).

Lee, L.G. et al., "New energy transfer dyes for DNA sequencing," *Nucl. Acids Res.* 25:2816–2822 (Jul. 1997).

Nelson, P.S. et al., "Oligonuleotide labeling methods 3. Direct labeling of oligonucleotides employing a novel, non–nucleosidic 2–aminobutyl–1,3–propanediol backbone," *Nucl. Acids Res.* 20:6253–6259 (1992).

Perkin–Elmer, ABI PRISM™ Dye Terminator Cycle Sequencing Ready Reaction Kit with AmpliTaq®DNA Polymerase, FS, Protocol. P/N 402078, Revision A (1995).

Perkin–Elmer Applied Biosystems, ABI PRISM® Big-Dye™ Primer Cycle Sequencing Ready Reaction Kit With AmpliTaq® DNA Polymerase, FS, Protocol, P/N 403057, Revision C (1997).

Perkin–Elmer Applied Biosystems, Automated DNA Sequencing, Chemistry Guide, P/N 4305080, Revision A (1998).

Picard, C. et al., "Detection and Enumeration of Bacteria in Soil by Direct DNA Extraction and Polymerase Chain Reaction," *Appl. Environmental Microbiol.* 58:2717–2722 (1992).

Prober, J.M. et al., "A System for Rapid DNA Sequencing with Fluorescent Chain–Terminating Dideoxynucleotides," *Science* 238:336–341 (1987).

Rosenblum, B.B. et al., "New dye–labeled terminators for improved DNA sequencing patterns," *Nucl. Acids Res.* 25:4500–4504 (Nov. 1997).

Ruano, G. et al., "Heat–Soaked PCR: An Efficient Method for DNA Amplification with Applications to Forensic Analysis," *BioTechniques* 13: 266–274 (1992).

Salas–Solano, O. et al., "Routine DNA sequencing of 1000 Bases in Less Than One Hour by Capillary Electrophoresis with Replaceable Linear Polyacrylamide Solutions," *Anal. Chem.* 70:3996–4003 (Oct. 1998).

Sanger, F. et al., "DNA sequencing with chain–terminating inhibitors," *Proc. Natl. Acad. Sci. USA* 74:5463–5467 (1997).

Sasaki, N. et al., "Transcriptional sequencing: A method for DNA sequencing using RNA polymerase," *Proc. Natl. Acad. Sci. USA* 95:3455–3460 (Mar. 1998).

Smith, L.M. et al., "The synthesis of oligonucleotides containing an aliphatic amino group at the 5' terminus: synthesis of fluorescent DNA primers for use in DNA sequence analysis," *Nucl. Acids Res.* 13:2399–2413 (1985).

Smith, L.M. et al., "Fluorescence detection in automated DNA sequence analysis," *Nature* 321: 674–679 (1986).

Steffens, D.L. and Roy, R., "Sequence Analysis of Mitochondrial DNA Hypervariable Regions Using Infrared Fluorescence Detection," *BioTechniques* 24:1044–1046 (Jun. 1998).

Voss, H. et al., "Direct genomic fluorescent on–line sequencing and analysis using *in vitro* amplification of DNA," *Nucl. Acids Res.* 17:2517–2527 (1989).

Wang, B. et al., "Large–Scale Preparation of Plasmid DNA by Microwave Lysis," *BioTechniques* 18:554–555 (1995).

Wilson, R.K. et al., "Optimization of Asymmetric Polymerase Chain Reaction for Rapid Fluorescent DNA Sequencing," *BioTechniques* 184:184–189 (1990).

Zakeri, H. et al., "Peak Height Pattern in Dichloro–Rhodamine and Energy Transfer Dye Terminator Sequencing," *BioTechniques* 25:406–414 (Sep. 1998).

Chadwick, N. et al., "Comparison of Three RNA Amplification Methods as Sources of DNA for Sequencing," *BioTechniques* 25:818–821 (Nov. 1998).

Perkin–Elmer Applied Biosystems, ABI PRISM® Big-Dye™ Terminator Cycle Sequencing Ready Reaction Kit With AmpliTaq® DNA Polymerase, FS, Protocol, P/N 4303237, Revision C (1998).

* cited by examiner

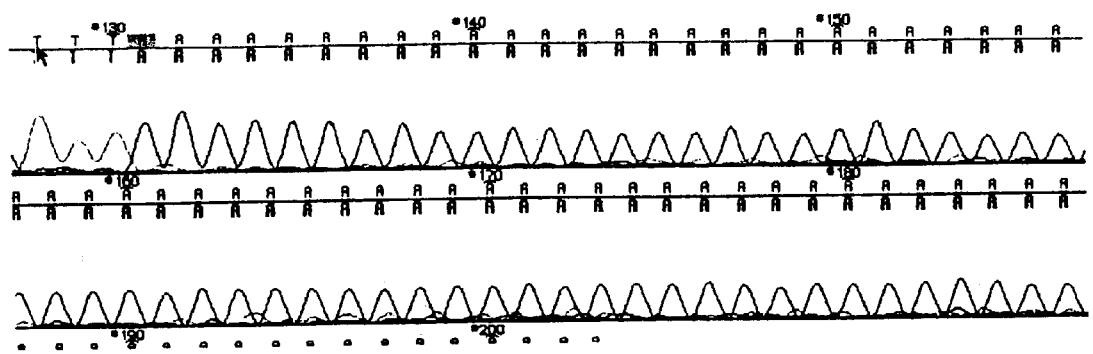
FIG. 3 RESOLUTION OF A LONG POLY-A TAIL

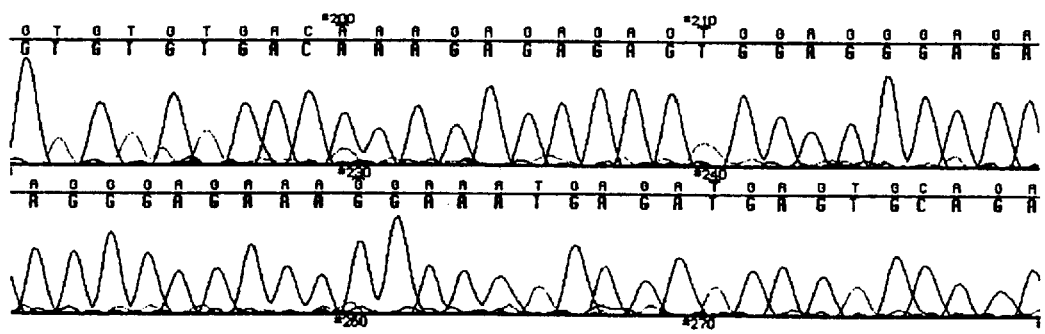
FIG. 4 RESOLUTION OF LOW-COMPLEXITY GENOMIC SEQUENCE

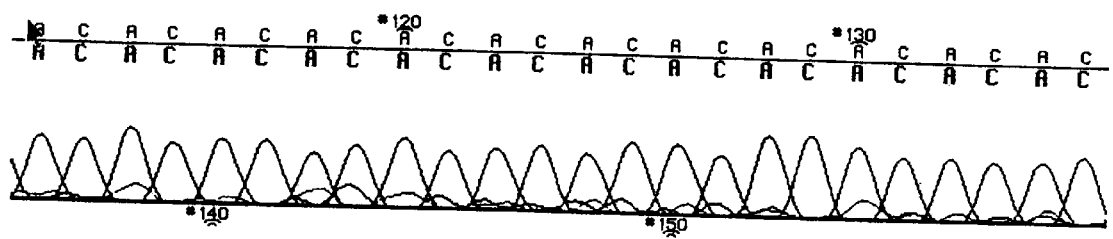
FIG. 5 RESOLUTION OF DINUCLEOTIDE REPEATS BY DBLS

5CFB-dR110

6CFB-dR6G

5CFB-dTMR

5CFB-dROX

DIRECT BACTERIAL LYSATE SEQUENCING

CROSS-REFERENCE TO RELATED APPLICATION

This application claims the benefit of the filing date of provisional application 60/124,676 filed on Mar. 16, 1999, which is herein incorporated by reference.

BACKGROUND OF THE INVENTION

1. Field of the Invention

The present invention relates to novel methods for sequencing nucleic acid molecules. More specifically, methods are provided for sequencing nucleic acid molecules present in bacterial lysates without the need to purify nucleic acid templates from highly soluble cellular components.

2. Related Art

The Sanger-dideoxy DNA sequencing method is currently the most widely used sequencing technique (Sanger, F. et al., *Proc. Natl. Acad. Sci. USA* 74:5463–5467 (1977), Smith, L. M. et al., *Nucleic Acids Res.* 13:2399–2412 (1985); Smith, L. M. et al., *Nature* 321:674–679 (1986), Voss, H. et al., *Nucleic Acids Res.* 17:2517–2527 (1989); Prober, J. M. et al., *Science* 238:336–341 (1987), Bergot, U.S. Pat. No. 5,366,860). The Sanger-dideoxy method combined with high-throughput, automated fluorescent sequencing machines and sophisticated DNA analysis by computers has allowed the sequencing of entire genomes (Fleischmann, R. D. et al., *Science* 269:496–512 (1995); Fraser, C. M. et al., *Science* 270:397–403 (1995); Himmelreich, R. et al., *Nucleic Acids Rev.* 24:4420–4449 (1996)).

The quality of the nucleic acid template used for automated fluorescent sequencing is integral to the success of the cycle sequencing reactions. The importance of high quality nucleic acid template has led to the development of both manual and robotic systems to generate nucleic acid template suitable for sequencing. However, large genome sequencing projects would benefit directly from reductions in the time and cost of nucleic acid template preparation.

Previous efforts using heat-soaked polymerase chain reaction (HS-PCR, Chen, Q. et al., *BioTechniques* 21:453–457 (1996)) or asymmetric polymerase chain reaction (Wilson, R. et al., *BioTechniques* 8:184–189 (1990)) have sacrificed data quality in order to eliminate or minimize the effort needed to purify nucleic acid template.

SUMMARY OF THE INVENTION

The present invention provides methods for sequencing nucleic acid molecules, referred to as Direct Bacterial Lysate Sequencing (DBLS), without the need to purify nucleic acid templates from cellular components present in bacterial cell lysates.

In one general aspect the invention provides methods for sequencing nucleic acid templates comprising the steps of lysing bacterial host cells to produce a bacterial cell lysate containing the nucleic acid template and sequencing the nucleic acid template present in the bacterial cell lysate. In a more specific aspect the nucleic acid template present in the bacterial lysate is not amplified by polymerase chain reaction (PCR) prior to sequencing. In another specific aspect the nucleic acid template is not separated from highly soluble cellular components (e.g., sheared low molecular weight chromosomal DNA, small RNA molecules, salts, nucleotides, nucleoside monophosphates, nucleoside diphosphates, nucleoside triphosphates, amino acids, small peptides, and small carbohydrates) prior to sequencing. In yet another specific aspect the method includes culturing the bacterial host cells containing the nucleic acid template prior to lysis.

The invention further provides methods for sequencing nucleic acid templates comprising the steps of lysing the bacterial host cells to produce a bacterial cell lysate containing the nucleic acid template and sequencing the nucleic acid template using a sequencing reaction and detectable label to detect the products of the sequencing reaction. In a more specific aspect the detectable label used for sequence product detection comprises a fluorescent dye.

Generally, the method used for sequencing the nucleic acid template will be one which employs a detection method for identifying a detectable label which allows for the detection of low concentrations of sequencing reaction products. Such detectable labels include high intensity fluorescent dyes, infrared dyes, and radioactive labels. High intensity fluorescent dyes include the d-rhodamine and fluorescein/d-rhodamine dyes having the structures shown in FIGS. 6A–6F, FIGS. 7A–7D, FIGS. 8A–8D, and FIGS. 9A–9D.

The nucleic acid templates present in the cell lysate may be separated from cellular debris and precipitated material by one method or a combination of methods (e.g., centrifugation) prior to sequencing. Further, these nucleic acid templates will generally be sequenced using thermal cycle sequencing, but, in an alternative aspect, may be amplified prior to sequencing. When PCR is used to amplify the nucleic acid templates, the amplified templates will generally be present in concentrations high enough so that any number of art known methods for sequencing nucleic acid may be used (e.g., thermal cycle sequencing, Maxam-Gilbert, Sanger sequencing, and exonuclease digestion sequencing).

More specifically, the invention relates to methods for directly sequencing nucleic acid templates in bacterial lysates in which cells of individual bacterial colonies, each harboring a vector containing identical nucleic acid templates, are removed from a plate containing solidified cultures and used to inoculate a liquid culture medium. The bacterial host cells in the liquid culture medium are allowed to multiply for a period of time, after which these cells are pelleted by centrifugation and washed to remove residual culture medium. The washed cells are then resuspended in an aqueous solution (e.g., water) and incubated at 90–98° C. for 5–30 minutes to induce cell lysis. The samples are then cooled either on ice or to room temperature and centrifuged. After centrifugation, the resulting lysates are used in cycle sequencing reactions. Preferably, the bacterial host cells are *E. coli* and are cultured in Luria broth or Terrific broth (TB) (Difco Laboratories).

In an additional aspect the nucleic acid template concentration present during the sequencing reaction is between about 15 ng and about 2 μg. As explained in detail below, a number of factors can be varied to change the amount of nucleic acid template present during the sequencing reaction (e.g., the bacterial host cell concentration from which the bacterial cell lysate is generated can be altered and the bacterial host cells can be lysed in varying volumes of lysis solutions).

In another aspect the present invention provides methods for sequencing nucleic acid templates comprising lysing bacterial host cells containing the nucleic acid templates to produce a cell lysate and forming in the cell lysate mixture of first, second, third, and fourth classes of polynucleotides. The polynucleotides in the first class have a 3'-terminal dideoxyadenosine, the polynucleotides in the second class have a 3'-terminal dideoxycytidine, the polynucleotides in the third class have a 3'-terminal dideoxyguanosine, and the polynucleotides in the fourth class have a 3'-terminal dideoxythymidine. Further, the polynucleotides in each of these classes are labeled with at least one detectable label. In one related aspect the nucleic acid template is not purified from highly soluble cellular components (e.g., sheared low molecular weight chromosomal DNA, small RNA molecules, salts, nucleotides, nucleoside monophosphates, nucleoside diphosphates, nucleoside triphosphates, amino acids, small peptides, and small carbohydrates) which are released from the bacterial host cells upon lysis. In another related aspect the nucleic acid template is not amplified by polymerase chain reaction prior to forming the mixture of polynucleotides. As above, the detectable label can be a fluorescent dye.

In yet another aspect the present invention provides methods for sequencing nucleic acid templates comprising hybridizing primers to the nucleic acid template, forming mixtures comprising the nucleic acid template, deoxyadenosine triphosphate, deoxycytidine triphosphate, deoxyguanosine triphosphate, and deoxythymidine triphosphate, DNA polymerase, and dideoxynucleosides, incubating the mixtures under conditions suitable for the synthesis of populations of DNA molecules complementary to portions of the nucleic acid template, and separating the synthesized DNA molecules by size so that at least a part of the nucleotide sequence of the nucleic acid template can be determined. Generally, the nucleic acid template which is sequenced is present in a cell lysate that is prepared by lysing bacterial host cells containing the nucleic acid template. Further, the nucleic acid template is generally not purified from highly soluble cellular components (e.g., sheared low molecular weight chromosomal DNA, small RNA molecules, salts, nucleotides, nucleoside monophosphates, nucleoside diphosphates, nucleoside triphosphates, amino acids, small peptides, and small carbohydrates) released from the bacterial host cells upon lysis and is not amplified by PCR prior to forming the mixture of polynucleotides. Again, as above, the detectable label can be a fluorescent dye.

The present invention also provides methods for sequencing nucleic acid molecules of cDNA and genomic libraries. According to these methods, as above, bacterial host cells containing specific cloned nucleic acid sequences are isolated, a cultured and then lysed. The nucleic acid templates present in the bacterial cell lysate will generally be either sequenced using thermal cycle sequencing or amplified by PCR and then sequenced by art known methods (e.g., thermal cycle sequencing, Maxam-Gilbert, Sanger sequencing, and exonuclease digestion sequencing). Alternatively, methods for sequencing nucleic acid templates other than thermal cycle sequencing could be used when templates are not amplified by PCR, if the detection method used is one with high sensitivity (e.g., detection methods which use high intensity fluorescent dyes).

In another aspect the invention provides methods for high-throughput sequencing of nucleic acid templates. The DBLS methods of the invention are readily adaptable for high-throughput sequencing of nucleic acid templates. Such methods are useful when large numbers of nucleic acid templates are sequenced as, for example, when the sequence of the genome of an entire organism is sought.

The high-throughput sequencing methods of the invention involve the automated processing of one or more steps of the DBLS methods. For example, individual colonies comprising host cells which contain identical nucleic acid templates may be identified on petri dishes by optical methods and automatically transferred into individual wells of a multi-well culture plate for further culture. Additionally, after a colony has been cultured to a suitable optical density, a mechanical device may be used to remove the culture medium from each well of the multi-well plate, add reagents to each well of the wells, and/or shift the incubation temperature to induce cell lysis.

BRIEF DESCRIPTION OF THE FIGURES

FIG. 3 shows the resolution obtained when DBLS is used to sequence a long polyA tail. Sequence data was obtained from a human cDNA clone generated by DBLS with BigDye™ terminator reaction chemistry and separated on an ABI PRISM 377XL.

FIG. 4 shows the resolution obtained when DBLS is used to sequence a genomic sequence of low-complexity. Sequence data was obtained from a mouse genomic clone generated by DBLS with BigDye™ terminator reaction chemistry and separated on an ABI PRISM 377XL.

FIG. 5 shows the resolution obtained when DBLS is used to sequence DNA having dinucleotide repeats. Sequence data was obtained from a human genomic clone generated by DBLS with BigDye™ terminator reaction chemistry and separated on an ABI PRISM 377XL.

DETAILED DESCRIPTION

Figure 1:
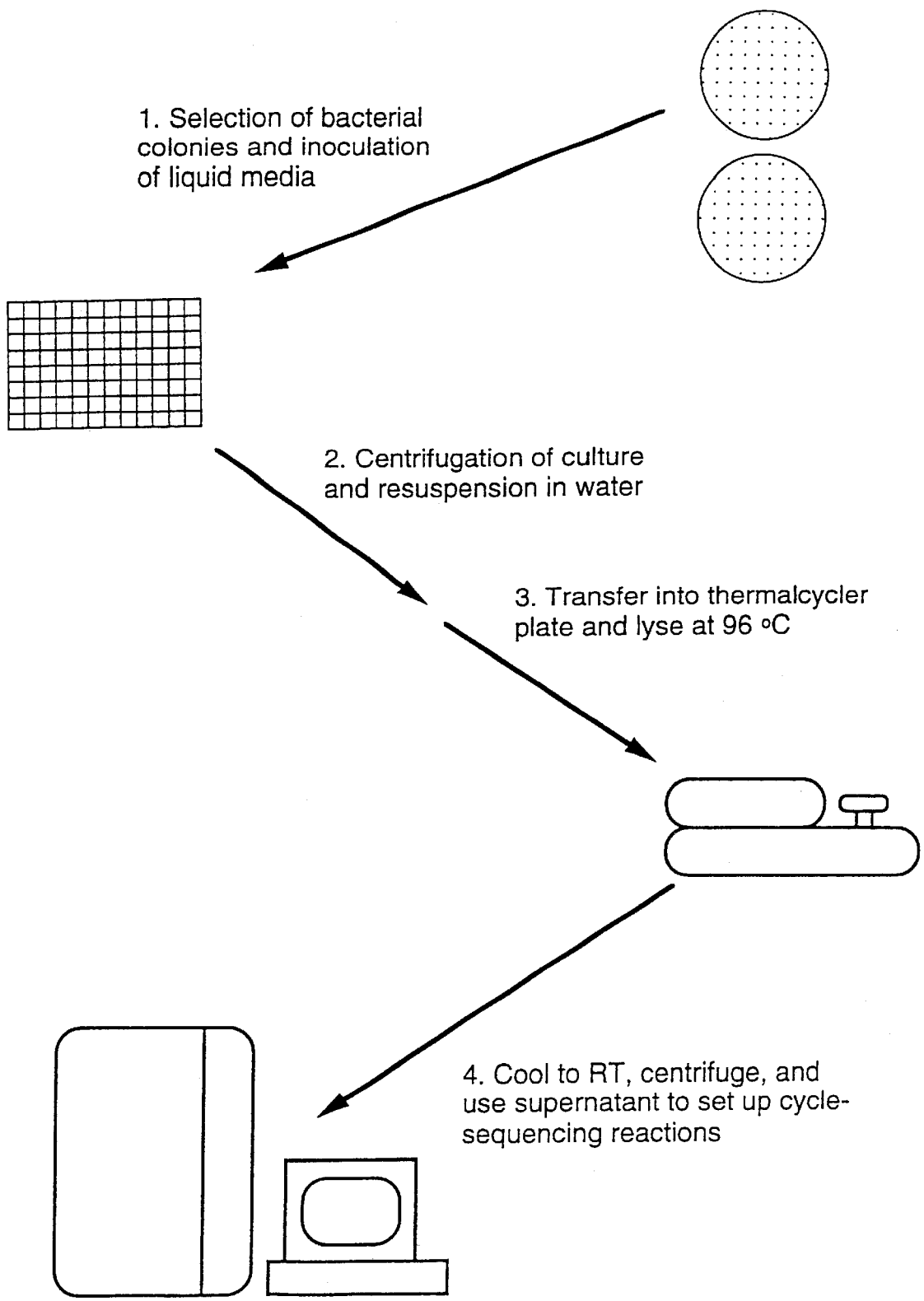
FIG. 1 shows one embodiment of the direct bacterial lysate sequencing method (DBLS). In step 1, bacterial colonies harboring plasmids are picked from plates containing a solidified culture medium and used to inoculate 96-well deep well plates containing liquid media. In step 2, the deep well plates are incubated overnight, the bacterial host cells are pelleted by centrifugation, and the media is decanted. In step 3, the bacterial host cell pellets are washed and resuspended in water prior to transfer into 96 well trays. The bacterial host cells are then lysed at about 96° C. for about 20 minutes to produce bacterial cell lysates. In step 4, the bacterial cell lysates are cooled to room temperature and centrifuged. The resulting supernatant is then used to perform cycle sequencing reactions.

The present invention provides a novel nucleic acid sequencing method which eliminates the preparation of nucleic acid template with little or no loss of data quality. In this procedure, a small volume of bacterial culture (e.g., 1.0 ml) is lysed and sequenced using standard protocols.

As both public and private sequencing programs increase their production level, the development of novel procedures and technologies are needed to minimize the equipment and personnel cost of these efforts. The Direct Bacterial Lysate Sequencing (DBLS) method eliminates one of the most costly and rate limiting aspects of the sequencing process, template purification, while achieving comparable or improved reaction success rates and average read lengths. The method is robust and can be used on the majority of vectors and host cell strains without loss of sequencing performance. Widespread implementation of DBLS should assist large sequencing centers to reduce costs and more rapidly generate sequencing data.

To streamline high-throughput expressed sequence tag (EST) sequencing process, the present invention was developed as a method of directly sequencing nucleic acid templates in bacterial lysates, thereby eliminating the need to purify these templates prior to sequencing. Using the DBLS method, it is possible to eliminate template purification while achieving equal or better quality sequencing data as compared to previously used methods.

A test set of human and plant cDNA clones were selected and sequenced using both standard PCR and plasmid template purification procedures, and by DBLS. The DBLS sequencing data was equal to or better than the data generated from the purified templates. Sequencing of difficult templates, including GC-rich regions, dinucleotide repeats, and long polyA tails, was possible using the DBLS method. (FIGS. 3–5.) The performance of the DBLS method was also tested on all widely used reaction chemistries, multiple cloning vectors, and several different host cell strains. The reaction chemistries tested included ones using terminators and primers linked to the following dye types: d-rhodamine dyes, BigDyes, and Energy-Transfer dyes (Amersham Pharmacia Biotech AB, SE-751 84 Uppsala, Sweden).

The results presented in Example 1 demonstrate the DBLS method is a cost effective and time saving alternative to the nucleic acid template purification procedures in use today.

Definitions

The following definitions are provided to clarify the subject matter which the inventors consider to be the present invention.

As used herein, the phrase "bacterial cell lysate" (also referred to as "cell lysate") refers to the mixture of cellular components and reagents which result from the lysis of bacterial host cells. In many instances, a major component of a bacterial lysate will be water. The term "bacterial cell lysate" also includes the mixture of cellular components and reagents which result from the lysis of bacterial host cells after a nucleic acid template has been separated from cellular materials which are relatively insoluble in aqueous solution (e g., cellular debris and high molecular weight chromosomal DNA).

As used herein, the phrases "bacterial cell line(s)" and "bacterial host cell(s)" refer to bacterial species and strains which are used to clone and amplify nucleic acid templates. These bacterial host cells include both the bacteria which contain the various nucleic acid molecules which make up the library and bacteria of clonal origin which contain identical, or nearly identical, copies of a single nucleic acid template. Thus, the phrase "bacterial cell line" and "bacterial host cell" include both bacteria which contain the nucleic acid molecules of a particular library and those of a single colony which are cultured and lysed to yield nucleic acid molecules for sequencing reactions. Examples of bacteria suitable for use as bacterial host cells include *Escherichia coli* and *Salmonella typhimurium*.

As used herein, the phrase "nucleic acid template" refers to nucleic acid molecules which are sequenced during the practice of the present invention. As one skilled in the art would recognize, cloned nucleic acid sequences are normally contained within vectors. The phrase "nucleic acid template" refers to cloned nucleic acid molecules and, in appropriate instances, vector sequences which are sequenced along with the insert. As one skilled in the art would also recognize, vector sequences are often used as reference markers for determining where the sequence of an insert begins.

Vectors suitable for use with the present invention include plasmids, cosmids, phage, chromosomes, filamentous single-stranded bacteriophages (e.g., λ, M13 and gIII) and other vehicles which allow for the insertion and propagation of nucleic acid sequences.

As used herein the phrase "linking group" (L) refers to a functionality capable of reacting with a "complementary functionality" (e.g., —SH and —NH$_2$) attached to a reagent, such reaction forming a "linkage" connecting a dye to a reagent. The particular linking group used depends on the nature of the complementary functionality and the type of linkage desired. In some cases, the linking group must be activated prior to reaction with a complementary functionality, e.g., the activation of a carboxylate linking group with dicyclohexylcarbodiimide and N-hydroxysuccinimide to form a N-hydroxysuccimide (NHS) ester. In one aspect whenever the complementary functionality is amine, the linking group of the invention is isothiocyanate, isocyanate, acyl azide, NHS ester, sulfonyl chloride, aldehyde or glyoxal, epoxide, carbonate, aryl halide, imidoester, carboduimide, anhydride, 4,6-dichlorotriazinylamine, or other active carboxylate. In another aspect whenever the complementary functionality is sulfhydryl, the linking group is haloacetyl alkyl halide, maleimide, halo acetyl, aziridine, acryloyl, arylating agent, e.g., fluorobenzene, and the like. When the complementary functionality is carboxylate, the linking group is generally diazoalane, diazoacetyl, carbonyldulmidazole, and carbodilmide (Hermanson). In one embodiment, the linking group is an activated NHS ester which reacts with an amine complementary functionality, where to form the activated NHS ester, a dye of the invention including a carboxylate linking group is reacted with dicyclohexylcarbodiimide and N-hydroxysuccinimide to form the NHS ester (Khanna, Kasai).

As used herein, the phrase "thermal cycle sequencing" refers to sequencing methods which involve repeated denaturation of double stranded nucleic acid templates followed by hybridization of the single stranded molecules to one, two, or more nucleic acid sequencing primers and the regeneration of the complementary nucleic acid strand in the presence of deoxynucleoside triphosphates and one, two or more dideoxynucleoside triphosphate. Generally, four separate reactions are perform ed, each of which occur in the presence of a different dideoxynucleoside triphosphate (e.g., ddATP, ddGTP, ddCTP, and ddTTP).

Whether a sequencing reaction is "successful" is determined by both the read length and the percent accuracy of the sequencing data obtained. As used herein, the term "success," when used in reference to sequencing reactions, refers to reactions which yield sequencing data that is greater than about 95% accurate over at least about 450 contiguous nucleotides. By "accurate" is intended that the sequencing data correctly reflects the nucleotide sequence of the nucleic acid template. For example, sequencing data which is 95% accurate would contain 5 errors over a stretch of 100 nucleotides of nucleic acid template.

The term "purified", as it is used in regards to nucleic acid templates, means that the nucleic acid templates is separated from cellular components which are of relatively high solubility in aqueous solution. Cellular components which have relatively high solubility in aqueous solution include sheared low molecular weight chromosomal DNA, small RNA molecules, salts, nucleotides, nucleoside, nucleoside monophosphates, nucleoside diphosphates, nucleoside triphosphates, amino acids, small peptides (i.e., 10 or fewer amino acids), and small carbohydrates (e.g., glucose and ribose). Further, nucleic acid templates which have been separated from materials which sediment during low speed, short duration centrifugation (e.g., 2135×g for 10 minutes) and ultrafiltration (e.g., filtration using filters having a pore size of 0.45 microns or greater) are not considered to be purified for the purposes on the present invention.

As used herein, the term "identical," as it is used in reference to a nucleic acid templates, refers to nucleic acid templates which are derived from bacterial host cells of clonal origin which have been separated from other bacterial cells in a population after acquiring a nucleic acid template. In other words, all or almost all of the cells of clonal origin will contain the same nucleic acid template molecule. Such cells, for example, include cells which have been transformed with a vector containing a nucleic acid insert and then cultured on a solid medium to isolate cells that are the progeny of a cell which acquired a single nucleic acid molecule. As one skilled in the art would recognize, variations in such molecules can occur as a result of processes such as nucleotide insertions, deletions and substitutions. For the purposes of the present invention, such molecules are considered to be "identical."

Overview

The present invention provides methods for sequencing nucleic acid molecules present in bacterial lysates without the need to purify the nucleic acid templates. The invention provides methods for sequencing nucleic acid templates comprising the steps of culturing bacterial host cells which contain the nucleic acid template, lysing the bacterial host cells to produce a bacterial cell lysate which contains the nucleic acid template, and sequencing the nucleic acid template present in bacterial cell lysate. In one aspect the nucleic acid template present in the bacterial lysate is not amplified by PCR prior to sequencing. In another aspect fluorescent labels are used to detect the sequencing reaction products. In an additional aspect a detection method is used which results in the generation of sequencing data that is greater than about 95% accurate over at least 450 contiguous nucleotides.

When nucleic acid templates are separated from components of the bacterial host cells during the practice of the invention, the separation methods used will generally be intended to separate the nucleic acid template from cellular components which are relatively insoluble in aqueous solution (e.g., cell wall materials, aggregated proteins, and high molecular weight chromosomal DNA). Thus, one separation method suitable for use in the practice of the invention is low speed, short duration centrifugation.

The method for performing DBLS disclosed in Example 1 incorporates a step where the bacterial lysate is incubated either at room temperature or on ice for about 5 minutes prior to centrifugation. This incubation step is intended to facilitate the precipitation of cellular material, without the addition of exogenous solutes, which is then pelleted during the centrifugation step. While the solute concentration in cell lysates will generally not be high enough to precipitate having relatively low molecular weight molecules (e.g., sheared low molecular weight chromosomal DNA, small RNA molecules, salts, nucleotides, nucleoside monophosphates, nucleoside diphosphates, nucleoside triphosphates, amino acids, small peptides, small carbohydrates, and the nucleic acid template), the solute concentration will generally be sufficient to result in the precipitation of high molecular weight molecules (e.g., proteins and high molecular weight chromosomal DNA).

The present invention also provides methods for sequencing nucleic acid templates derived from cDNA and genomic libraries. As above, cells containing a specific cloned nucleic acid template are isolated, cultured and then lysed. The nucleic acid templates present in the lysate are then sequenced.

One embodiment of the invention is shown in FIG. 1. This embodiment is discussed in detail in Example 1. In brief, bacterial colonies harboring plasmids which contain nucleic acid inserts are picked from plates and used to inoculate individual wells of 96-well deep well plates containing liquid media (e.g., Luria broth). The cultures in the well plates are grown overnight, the bacteria are washed by centrifugation and resuspended in water prior to transfer into 96 well PCR trays. After resuspension in water, the bacterial cells located in the wells are lysed at about 96° C. for about 20 minutes. The samples are cooled and centrifuged, and the resulting lysates are then used to perform cycle sequencing reactions.

The inventors have found that it is not necessary to include chemical agents (e.g., non-ionic or ionic detergents, lysozyme, buffers, salts, RNAses, DNAse inhibitors) in the lysis solution, and thermal lysis of host cells resuspended in water yields nucleic acid templates which are suitable for sequencing.

As one skilled in the art would recognize, a considerable number of modifications of this embodiment can be made. As explained in detail below, the inventors have optimized conditions for performing DBLS with small numbers of nucleic acid templates and as part of high-throughput sequencing protocols. Thus, the sequencing methods of the present invention have the advantage of being amendable to high-throughput sequence analysis of large numbers of nucleic acid templates. Further, these sequencing methods can be performed relatively quickly and can be designed to use small amounts of reagents.

Sources of Nucleic Acid Templates

While the sequencing methods of the invention can be used to sequence a single nucleic acid template, these methods are especially useful for sequencing large numbers of template molecules derived from complex cDNA and genomic libraries (e.g., libraries derived from vertebrate cells).

A considerable number of clones are used when attempts are made to sequence the entire genome of an organism. The present invention provides a high-throughput method which is readily adaptable for sequencing large numbers of nucleic acid templates present in the clones of such libraries. This is so regardless of whether the library is derived from an organism or virus which has a relatively small (e.g., 1,500,000 base pairs) or a relatively large (e.g., 3,000,000,000 base pairs) genome.

The nucleic acid templates sequenced according to the methods of the invention may be obtained from various sources. These sources include virtually any organism, including DNA and RNA viruses and plants. Libraries which contain sequences of a wide variety of organisms are publicly available. See, e.g., *ATCC/NIH Repository Catalogue of Human and Mouse DNA Probes and Libraries*, Eighth Edition (1994), pages 156–157. Examples of libraries available from the American Type Culture Collection include Bacillus subtilis (ATCC No. 37356), *Caenorhabditis elegans* (ATCC No. 77366), human fetal brain (ATCC No. 77435), mouse embryo (ATCC No. 37484), and *Schizosaccharomyces pombe* (ATCC No.77293). In addition, libraries may be generated from organisms using art known techniques. Ausubel, F. M. et al., Current Protocols in Molecular Biology, John Wiley & Sons, Inc., New York, N.Y. (1993), for example, describes methods for producing cDNA and genomic libraries in Chapters 5 and 6.

As one skilled in the art would recognize, vectors suitable for use with the present invention will contain cloning sites near sequences to which sequencing and PCR amplification primers can hybridize. Suitable vectors will generally also contain appropriate selection markers and one or more origins of replication. Vectors for constructing plasmid based libraries include plasmids such as those capable of replication in *E. coli* such as, for example, pBR322, ColE1, pSC101, pUC-vectors (pUC 18, pUC 19, etc.: In: *Molecular Cloning, A Laboratory Manual*, Cold Spring Harbor Laboratory Press, Cold Spring Harbor, N.Y. (1982); and Sambrook et al., In: Molecular Cloning A Laboratory Manual (2d ed.) Cold Spring Harbor Laboratory Press, Cold Spring Harbor, N.Y. (1989)). Bacillus plasmids include pC194, pC221, and pC217. Such plasmids are disclosed by Glyczan, T. In: *The Molecular Biology Bacilli*, Academic Press, York (1982), 307–329. Suitable Strepioniyces plasmids include pIJ101 (Kendall et al., *J. Bacteriol.* 169:4177–4183 (1987)). Pseudomonas plasmids are reviewed by John et al., (*Rev. Infec. Dis.* 8:693–704 (1986)), and Igaki, (*Jpn. J. Bacteriol.* 33:729–742 (1978)). Broad-host range plasmids or cosmids, such as pCP13 (Darzins and Chakrabarty, *J. Bacteriol.* 159:9–18 (1984)) can also be used for the present invention.

Additional vectors suitable for use in bacteria include pQE70, pQE60 and pQE-9, available from Qiagen, pBS vectors, Phagescript vectors, Bluescript vectors, pNH8A, pNH16a, pNH18A, pNE46A, available from Stratagene; ptrc99a, pKK223-3, pKK233-3, pDR540, pRIT5 available from Pharmacia; and λZapII, λgt10, λgt11, and λgt22A. Other suitable vectors would be recognized by one skilled in the art.

Introduction of constructs into bacterial cells can be effected by art known techniques such as calcium phosphate transfection, DEAE-dextran mediated transfection, cationic lipid-mediated transfection, electroporation, transduction, and infection. Such methods are well known in the art and are described in many standard laboratory manuals (e.g., Davis et al., *Basic Methods In Molecular Biology* (1986)).

Cell Culturing and Washing Methods

Microorganisms containing the nucleic acid template to be sequenced will generally be grown to amplify the number of template nucleic acid molecules.

These microorganisms can be cultured either in a liquid culture medium, often referred to as a "broth," or on the surface or sub-surface of a culture medium which has been solidified with a gelling agent such as agar-agar. Thus, both solid and liquid media can be used with the present invention to amplify the nucleic acid templates.

Solid culture media will be used in most instances to isolate cells which contain identical nucleic acid templates (e.g., to isolate bacterial host cells that contain the individual vectors of the library) and liquid media will generally be used to culture cells for the amplification of specific nucleic acid templates. However, cells containing identical nucleic acid templates may also be removed directly from the surface of a solid medium (e.g., solid medium in a petri dish). Thus, solid media may also be used to culture cells for the amplification of specific nucleic acid templates.

A considerable number of culture media suitable for use in the practice of the present invention are known in the art. Many of these media are described in *ATCC Catalog of Bacteria and Bacteriophages*, 18th Edition (1992), Sambrook, J. et al., eds., *Molecular Cloning, A Laboratory Manual*, 2nd. edition, Cold Spring Harbor Laboratory Press, Cold Spring Harbor, N.Y. (1989), and Celis, J., ed., *Cell Biology*, Academic Press, $^2$nd edition, (1998). One example of a culture medium suitable for culturing *E. coli*, as well as other bacteria, is Luria broth (LB). See Luria, S. E., and Delbruck, M., *Genetics* 28:491–511 (1943).

The culture medium used with the present invention will vary with the nutritional requirements of the microorganism which contains the template nucleic acid, as well as a variety of other factors (e.g., culture aeration, cell density desired, the cost of the medium components, and selection markers used).

One consideration in the selection of a culture medium is that the nucleic acid template concentration must be high enough to allow for both sequencing and detection of the sequencing reaction products. As one skilled in the art would recognize, a bacterial host cell culture which contains relatively few cells can be used in the practice of the present invention when a relatively large volume of culture is used. Similarly, a variety of factors other than choice of culture medium can be used to obtain a culture containing a suitable number of cells for direct sequencing of nucleic acids in bacterial cell lysates. These factors include the incubation time of the bacterial host cell culture, the size of the initial innoculum, the amount of time and the temperature at which the culture is incubated, and the copy number of the vector which contains the nucleic acid template. Example 1 provides an example of culture conditions suitable for use in the practice of the present invention.

A second factor to be considered when choosing a culture medium for growth of the bacterial host cells is the amount of interference with the sequencing reaction which can be tolerated. The inventors have determined that growth of the bacterial host cells in certain culture media results in a reduction of interference from media components. The inventors have also found that washing the bacterial host cells prior to lysis and using a high concentration of nucleic acid templates can decrease background and allow for longer read lengths.

The inventors have tested the DBLS system with a number media types for culturing bacterial host cells. In generally, when host cells are cultured in highly enriched, undefined media (e.g., TB and NZCYM), higher background is detected during the sequencing reactions than when host cells are cultured in relatively unenriched, undefined culture media (e.g., LB). Specifically, sequencing data derived from nucleic acid templates obtained from host cells cultured in TB and NZCYM had two to three times the background of sequencing data derived nucleic acid templates obtained from bacterial host cells cultured in LB. However, this background can be removed with additional washing steps.

The term "background", as used herein, refers to overlapping and/or ambiguous signals which can interfere with the analysis of sequence data and obscure the identification of the correct bases in nucleic acid molecules.

As noted above, washing of the bacterial cells prior to lysis was also found to improve the sequencing results by reducing the background level. In the method disclosed below in Example 1, the bacterial host cells are washed twice with water prior to cell lysis. The use of water as a washing solution removes medium components which potentially could interfere with sequencing reaction and does not introduce additional potentially interfering compounds (e.g., salts).

As part of the process for washing the bacterial host cells disclosed in Example 1, the cells are separated from the culture medium by centrifugation. When the bacterial host cells are cultured in liquid medium and separated from the culture medium by centrifugation, the speed of this centrifugation and the amount of time the solutions containing host cells are centrifuged will vary with factors such as the type or centrifugation rotor used and the container that the host cells are centrifuged in.

The objects of the centrifugation are to rapidly provide a host cell pellet which is sufficiently solid to allow for the removal of the supernatant with minimal host cell loss. One factor to be considered when selecting centrifugation speed and duration is that the recommended specifications of either the rotor or the sample container(s) should not be exceeded. As shown in Example 1, the inventors have found that, using 96 well plates for the culture and washing of host cells, centrifuged at about 2135×g for about 10 minutes results in the formation of bacterial host cell pellets which are sufficiently solid to allow for the removal of liquid supernatant with minimal host cell loss.

The bacterial host cell cultures of the invention, however, can be harvested and washed by methods other than centrifugation. One alternative method is ultra-filtration. A number of manufacturers produce filtration media which are suitable for harvesting and washing bacterial host cells. Generally such filters have a pore size of 0.45 $\mu$M or less. One series of filters suitable for use in harvesting and washing bacterial cells are the MF series available from Millipore Corporation, 80 Ashby Road, Bedford, Mass., 01730-2271.

As already indicated, the present invention is adaptable for high-throughput sequencing of nucleic acid templates. To achieve high-throughput sequencing, it is best to house the cultures of microorganisms on a multicontainer carrier or platform. A multicontainer carrier facilitates the growth of a plurality of individual cultures simultaneously. In one embodiment, a multi-well microplate, for example a 96 or a 384 well microplate, which can accommodate 96 or 384 different cultures, is used as the carrier. Such multi-well microplates are both known in the art and commercially available. Sigma Chemical Co., *Biochemical Organic Compound And Diagnostic Reagents*, 1996 Catalog, pages 2134; MJ Research, Inc. Watertown, Mass. 02472.

In this embodiment, individual cultures are contained in each well of a multi-well microplate. Each of these individual cultures consisting of bacterial host cells which contain identical nucleic acid templates. The bacterial host cells located in the wells of these plates are lysed and the nucleic acid templates present in the cell lysates are then sequenced. As above, the cell lysates may be subjected to further processing prior to sequencing (e.g., centrifugation and precipitation).

This embodiment of the invention is readily amendable to high-throughput processing of nucleic acid templates, which is highly desirable when large numbers of nucleic acid templates are sequenced. One reason the present invention is amendable to high-throughput sequencing is because optical devices are known in the art which can identify colonies on solid culture media. Misaka et al., U.S. Pat. No. 5,117,461, for example, describes a device for the automated counting of colonies. Once colonies are identified on a solid culture medium, for example, an automated device can readily be designed to remove cells of this colony and transfer them to a container of culture medium. Such a device can, for example, remove numerous colonies from one or more petri dishes containing solid culture media and transfer cells of these colonies to separate wells of a multi-well plate containing a liquid culture medium.

Cells Lysis Methods

Generally, methods for releasing nucleic acid molecules from cells for sequencing and library construction involve lysing the cells with alkali, heat, enzymes, or a combination of these agents. These methods include alkaline lysis, using sodium hydroxide and sodium dodecyl sulphate, and lysis methods employing, for example, enzymatic digestion followed by osmotic shock. Several methods for lysing bacterial cells are described in Wan et al., U.S. Pat. No. 5,837,529, Down et al, U.S. Pat. No. 5,766,852, Keating et al., U.S. Pat. No. 5,185,242.

Non-mechanical methods for lysing bacterial host cells are generally used because mechanical methods, while known in the art, often are not well suited for the recovery of nucleic acid templates which are suitable for sequencing. Mechanical methods suitable for lysing bacterial host cells to obtain nucleic acid molecules are disclosed in Wan et al., U.S. Pat. No. 5,837,529. These methods employ static mixers to lyse cells containing plasmids and can be scaled up to large volumes of cells. The methods disclosed in Wan et al. are designed to simplify the process of releasing plasmids from large numbers of bacterial host cells with minimal damage to plasmid DNA.

As suggested above, in general, the use of chemical agents and temperature shifts for inducing cell lysis are more suited for use with the present invention because methods employing these agents are more readily adaptable to high-throughput sequencing of nucleic acid templates and are less likely to shear nucleic acid molecules. Further, the use of chemical agents and temperature shifts for lysing bacterial host cells are more adaptable to high-throughput methods than mechanical lysis means because automated devices can be readily designed to add reagents to wells of multi-well culture plates and to shift the temperature of such plates.

As explained below in Example 1, the inventors have found with *E. coli* that thermal lysis of host cell suspensions by raising the temperature to about 96° C. for about 20 minutes insures complete bacterial lysis and plasmid denaturation without degrading the templates.

The inventors have found that nucleic acid templates suitable for sequencing by high-throughput and other means can be obtained when host cells are resuspended and lysed in water. Thus, it is not necessary to include chemical agents such non-ionic or ionic detergents, buffers, salts, RNAses, DNAse inhibitors in the lysis solution to obtain nucleic acid templates suitable for sequencing.

In addition, when thermal host cell lysis is performed, it is not necessary to use agents which weaken or degrade host cell walls prior to or during lysis. Commonly used method methods for weakening or degrading host cells walls involve digestion with enzymes and enzyme mixtures that break down cell wall components. One such enzyme is lysozyme. The inventors have thus found that the use enzymes and enzyme mixtures which break down host cell wall components (e.g., lysozyme) are not necessary in the practice of the present invention.

One additional advantage of thermal host cell lysis is that it can be used in the practice of the present invention without employing specialized equipment such as microwave ovens. (See Wang et al., *BioTechniques* 18:554–555 (1995); Hultner et al., *BioTechniques* 16:990–992, 994 (1994), Picard et al., *Appl. Environ. Micro.* 58:2717–2722 (1992).) In other words, conditions suitable for thermal, host cell lysis can be prepared using standard laboratory equipment such as water baths and heat blocks, in addition to the use of more specialized equipment (e.g., microwave ovens).

Sequencing Methods

The nucleic acid molecules present in the cell lysate may be sequenced by any number of methodologies (e.g., Maxam-Gilbert sequencing, Sanger sequencing, and exonuclease digestion sequencing). Generally, in the practice of the present invention either PCR amplified nucleic acid template will be sequenced or thermal cycle sequencing methods will be used. Further, thermal cycle sequencing can be done on PCR amplified nucleic acid templates. Preferably, according to the invention, thermal cycle sequencing will be performed on a nucleic acid template which has not been PCR amplified just prior to sequencing.

A number of methods for sequencing nucleic acid templates are known in the art. These include Maxam-Gilbert sequencing, Sanger sequencing, primer extension mass spectroscopy sequencing, and exonuclease digestion sequencing. In brief, Sanger sequencing is based on the principle that DNA polymerase will incorporate 2',3'-dideoxynucleotides into nucleic acid chains resulting in chain termination (Sanger et al., *Proc. Natl. Acad. Sci. USA* 74:5463 (1977)). Maxam-Gilbert sequencing is based on the principle that certain chemical reagents will catalyze strand breakage at specific nucleotides (Maxam, A. and Gilbert, W., *Methods in Enzymology* 65:499–599 (1980)). Both of these methods are reviewed in detail in Ausubel, F. M. et al., *Current Protocols in Molecular Biology*, John Wiley & Sons, Inc., New York, N.Y. (1993), Chapter 7.

The method developed by Sanger is referred to as the dideoxy chain termination method. In the most commonly used variation of this method, a DNA segment for which the sequence is desired is cloned into a single-stranded DNA phage, such as M13. These phage DNAs can serve as templates for the primed synthesis of the complementary strand by the Kienow fragment of DNA polymerase I. The primer is either a synthetic oligonucleotide or a restriction fragment isolated from the parental recombinant DNA that hybridizes specifically to a region of the M13 vector near the 3' end of the cloned insert. In each of four sequencing reactions, the primed synthesis is carried out in the presence of enough of the dideoxy analog of one of the four possible deoxynucleotides so that the growing chains are randomly terminated by the incorporation of these "dead-end" nucleotides. The relative concentration of dideoxy to deoxy forms is adjusted to give a spread of termination events corresponding to all the possible chain lengths that can be resolved by gel electrophoresis. The products from each of the four primed synthesis reactions are then separated on individuals tracks of polyacrylamide gels by the electrophoresis. Tags incorporated in the growing chains are used to develop an autoradiogram image of the pattern of the DNA in each electrophoresis track. The sequence of the deoxynucleotides in the cloned nucleic acid template is determined from an examination of the pattern of bands in the four lanes.

As noted above, the method developed by Maxam and Gilbert uses chemical treatment of DNA to generate size-nested sets of DNA fragments analogous to those produced by the Sanger method. Single or double-stranded DNA, labeled with radioactive phosphate at either the 3' or 5' end, can be sequenced by this procedure. In four sets of reactions, cleavage is induced at one or two of the four nucleotide bases by chemical treatment. Cleavage involves a three-stage process: modification of the base, removal of the modified base from its sugar, and strand scission at that sugar. Reaction conditions are adjusted so that the majority of end-labeled fragments generated are in the size range (typically 1 to 400 nucleotides) that can be resolved by gel electrophoresis. The electrophoresis, autoradiography, and pattern analysis are carried out essentially as is done for the Sanger method. Although the chemical fragmentation necessarily generates two pieces of DNA each time it occurs, only the piece containing the end label is detected on the autoradiogram.

While the Maxam-Gilbert and Sanger sequencing methods have traditionally been used in the art, a number of other methods for sequencing nucleic acid molecules have also been developed. One example of such a method is thermal cycle sequencing. While modifications of the thermal cycle sequencing method exist, this sequencing method normally involves the use of solutions containing a nucleic acid sequencing primer, deoxynucleoside triphosphates, one or more dideoxynucleoside triphosphates, a suitable buffer solution, a thermal stable DNA polymerase (e.g., *Thermus aquaticzis* DNA polymerase (*Taq*)), and the nucleic acid template to be sequenced. Denaturation of the extended primer from the nucleic acid template is achieved by periodic heating after periods at lower temperatures during which primer extension occurs. When a non-thermostable DNA polymerase is not used, the polymerase must be re-added to the solution after each heating step. For example, when temperatures are cycled between 37° C. and 95° C., non-thermostable enzymes, such as T7 DNA polymerase or Klenow fragment of DNA polymerase I, are denatured and must be added after each time the temperature is raised to 95° C. In contrast, *Taq* is stable to heating at 95° C. and, thus, no additional enzyme need be added for each cycle. A number of variations of the thermal cycle sequencing method are described in Fuller, U.S. Pat. No. 5,432,065, Oommen et al., U.S. Pat. No. 5,723,298, Fuller, U.S. Pat. No. 5,756,285, Mitchell et al., U.S. Pat. No. 5,817,797, and Brenner et al., U.S. Pat. No. 5,831,065.

Another method for sequencing nucleic templates is disclosed in Reeve et al., U.S. Pat. No. 5,849,542. This sequencing method employs primer extension mass spectroscopy to generate an observed mass spectrum. Further, Koster, U.S. Pat. No. 5,851,765 discloses methods for sequencing nucleic acid templates using exonuclease degradation and mass spectrometry. More specifically, the sequence of nucleic acid molecules is determined by cleaving the nucleic acid at one end with an exonuclease activity and identifying the sequentially released nucleotides by mass spectrometry. Each of these methods for sequencing nucleic acid templates, as well as numerous other methods, may be used in the practice of the present invention.

Another method for sequencing nucleic acid templates is described in Sasaki et al., *Proc. Natl. Acad. Sci. USA* 95:3455–3460 (1998). This method is based on an RNA polymerase catalyzed chain termination reaction which occurs in the presence of rhodamine dye attached to 3'-deoxynucleoside triphosphate (3'-dNTP). The method of Sasaki et al. is disclosed as a method which allows for rapid isothermal sequencing reaction in less than 30 minutes in the presence of low concentrations of nucleic acid template. Sasaki et al. also state that their method permits PCR direct sequencing without the need to remove PCR primers and 2'-dNTPs prior to sequencing. Finally, Sasaki et al. suggest that the disclosed sequencing method may be useful for large-scale sequencing in genome projects and clinical diagnosis.

Heat-soaked PCR (HS-PCR) can also be used to amplify nucleic acid templates prior to sequencing. With HS-PCR, reagents for sequencing the nucleic acid template are added to a reaction mixture containing the template after the temperature has been raised to a point where strand separation occurs (e.g., 95° C.). Ruano et al., *BioTechniques* 13:266–274 (1992) describe a method for performing HS-PCR for enhancing DNA amplification. According to this method, the nucleic acid sample is heated to 94° C. in 90 microliters of a 1.1×buffer for 30 minutes, followed by the addition of 10-microliters of concentrated (10×) deoxynucleotides, *Taq* DNA polymerase and primers prepared just prior to thermal cycling. Thermal cycling then proceeds as with standard PCR amplification methods.

Chen, Q. et al., *BioTechniques* 21:453–457 (1996) describe a variation of HS-PCR where DNA is directly sequenced in a bacterial cell lysate. According to this method, bacterial cells are pretreated with proteinase K and then lysed at 95° C. for 15 minutes. The cell lysate is centrifuged and the supernatant is then heated to 94° C. for 30 minutes. Sequencing reagents are added to the lysate and cycle sequencing commences using 30 cycles of 96° C. for 10 second, 50° C. for 5 seconds and 60° C. for 4 minutes. The quality of the sequencing data obtained by this method appears to be quite variably.

One problem with HS-PCR is that it is not readily amendable to high-throughput methods for producing nucleic acid templates. This is so because nucleic acid molecules which are amplified by this method the temperature must be raised to or near 94° C. prior to and while PCR reagents are added and it would be difficult to maintain such temperatures for large numbers of samples while adding reagents in a timely manner.

A high-throughput method for the preparation of single-stranded template DNA suitable for sequence analysis using fluorescent labeling chemistry is described in Wilson et al., *BioTechniques* 8:184–189 (1990). This method employs an asymmetric polymerase chain reaction to amplify recombinant plasmids and bacteriophage DNA directly from colonies and plaques. Due to the use of amplification primers located at least 200 base pairs 5' to the site where the sequencing primer anneals, the need for extensive purification of the asymmetric polymerase chain reaction product is alleviated. Instead, the single-stranded product DNA is directly sequenced using fluorescent dye-labeled oligonucleotides following precipitation with ethanol.

As noted above, one advantage of the methods of the present invention is that the nucleic acid template need not be purified prior to sequencing. Most sequencing methods require that the nucleic acid template which is sequenced be present in relatively pure form. Thus, after a nucleic acid template has been amplified either in a host cell or by PCR, the template is separated from potentially interfering materials (e.g., PCR primers).

Methods used to purify the nucleic acid template in the art-described sequencing methods include column chromatography (e.g., ion exchange and size exclusion chromatography), ethanol precipitation, cesium chloride/ethidium bromide density gradient centrifugation, phenol chloroform extraction followed by ethanol precipitation, and agarose gel electrophoresis. A number of these methods are discussed in Ausubel, F. M. et al., *Current Protocols in Molecular Biology*, John Wiley & Sons, Inc., New York, N.Y. (1993), Chapters 1 and 7.

Sequencing Product Detection

Once a sequencing reaction has been performed on a nucleic acid template, determination of the sequence of the molecule requires that the reaction products be identified. This identification process normally involves separation of the reaction products using electrophoretic procedures. Generally the electrophoretic matrix is of a type which is crosslinked or uncrosslinked polyacrylamide having a concentration (weight to volume) of between about 2–20 weight percent and contains a strand separating, or denaturing, agent, e.g., urea, formamide, and the like. Detailed procedures for constructing such matrices are provided in Ausubel, F. M. et al., "Current Protocols in Molecular Biology" John Wiley & Sons, Inc., New York, N.Y. (1993), Chapter 7; see also, *ABI PRISM™ 377 DNA Sequencer User's Manual, Automated DNA Sequencing Chemistry Guide*, Part No.4305080 (July 1998), *GeneScan® Reference Guide-Chemistry Reference for the ABI PRISM® 377 and ABI™ 373 Genetic Analyzer*, Part No. 4303188 (1997) both of which are available from Perkin Elmer/Applied Biosystems Inc. The optimal polymer concentration, pH, temperature, concentration of denaturing agent, employed in a particular separation depends on many factors, including the size range of the nucleic acids to be separated and their base compositions. Accordingly, application of the invention may require standard preliminary testing to optimize conditions for particular separations.

After sequencing reaction products have been separated from each other, the products must be identified in a manner which allows one to determine the sequence of the nucleic acid template. A considerable number of detection methods are known in the art. These methods generally involve the detection of "tags" comprising radionucleotide, fluorescent, infrared, or chemiluminescent labels or the use of nuclear magnetic resonance (NMR), mass spectroscopy, or multiplex detection methods. Further, combinations of these detection methods can be used. A number of methods for detecting reaction products are described in Ausubel, F. M. et al., *Current Protocols in Molecular Biology*, John Wiley & Sons, Inc., New York, N.Y. (1993), Chapter 7, Reeve et al., U.S. Pat. No. 5,849,542; Koster, U.S. Pat. No. 5,851, 765; and PCT publications WO 98/14612, WO 97/20949, WO 97/49769, WO 97/13810, WO 97/40104, and WO 97/36960.

A. Fluorescent Detection

A number of fluorescent methods for the detection of nucleic acid molecules have been developed. Smith et al., U.S. Pat. No. 5,821,058, for example, describes processes for the electrophoretic analysis of DNA fragments produced by DNA sequencing reactions. According to the described method, chromophores or fluorophores are used to tag the DNA fragments produced by the sequencing chemistry and permit the detection and characterization of the fragments as they are resolved by electrophoresis through a gel. Further described are methods in which four different fragment sets are tagged with the fluorophores fluorescein, Texas Red, tetramethyl rhodamine, and 7-nitrobenzofurazan and the location of bands representing the tagged DNA fragments is determined as the fragments are separated by electrophoresis.

High intensity labels for use in nucleic acid sequencing reactions are currently available and represent one of the most recent advances in nucleic acid detection technology. Ju et al., *Proc. Natl. Acad. Sci. USA* 92:4347–4351 (1995) were among the first to disclose the use of fluorescence energy transfer dye-labeled primers for DNA sequencing and analysis. More specifically, Ju et al. discloses fluorescent dye-labeled DNA primers which use fluorescence energy transfer (ET) to optimize the absorption and emission properties of the fluorescent label. The ET efficiency of the disclosed primers ranges from 65% to 97%. The fluorescence of the disclosed ET primers and the DNA sequencing products generated using these primers is 2- to 6-fold greater than that of single dye labeled nucleic acid primers and fragments. Due to the higher fluorescence intensity, the use of ET primers allows for DNA sequencing with DNA sample sizes which are one-fourth of that of previous systems. Ju et al. found that the disclosed ET primers could be used to generate high quality sequence out to at least 500 base pairs.

Hung et al., *Anal. Biochem.* 255:32–38 (1998), provide a comparison between the relative acceptor fluorescence emission intensity and the amount of residual donor fluorescence emission of fluorescence of energy transfer (ET) primers used in DNA sequencing reactions having different donor and acceptor dye combinations. Hung et al. synthesized primers having the following donor/acceptor pairs: 6-carboxyfluorescein/6-carboxy-X-rhodamine (FAM-ROX), 3-($\epsilon$-carboxypentyl)-3'-ethyl-5,5'-dimethyloxacarbocyanine/6-carboxy-X-rhodamine (CYA-ROX), and the 4,4-difluoro-4-bora-3α,4α-diaza-s-indacene-3-propionic acid (BODIPY) derivatives, 5,7-dimethyl-BODIPY/5-(4-phenyl-1,3-butadienyl)BODIPY (BODIPY503/512-BODIPY581/591). Additional ET primers are disclosed in Hung et al., *Anal. Biochem.* 252:78–88 (1997).

Two dye sets which are disclosed as being useful for automated dye-labeled terminator DNA sequencing are described in Rosenblum et al., *Nucleic Acids Res.* 25:4500–4504 (1997) and Lee et al., *Nucleic Acids Res.* 25:2816–2822 (1997). One of these dye sets consists of four separate 4,7-dichlororhodamine dyes. The other dye set consists of energy-transfer dyes which are conjugates comprising a 5-carboxy-d-rhodamine dye as an acceptor dye which is covalently linked to a 5- or 6-carboxy isomer of 4'-aminomethylfluorescein as a donor dye. Both of these dye sets utilize a linker between the dye and the nucleotide, and both provide peak heights in terminator sequencing which are more even than those provided by dye-terminators consisting of unsubstituted rhodamine dyes. This second dye set is disclosed as being especially suited for sequencing of high molecular weight DNA templates. (See also Hung et al., *Anal. Biochem.* 243:15–27 (1996); Hung et al., *Anal. Biochem.* 238:165–170 (1996); Lee et al., U.S. Pat. No. 5,847,162; PCT publication WO 97/49769; and *ABI PRISM*™ 377 *DNA Sequencer User's Manual, Automated DNA Sequencing Chemistry Guide*, Part No. 4305080 (July 1998)).

In one aspect of the invention, 4,7-diclororhodamine dye compounds having the general structure shown below as Formula I are used to detect sequence reaction products. (Note that all molecular structures provided throughout this disclosure are intended to encompass not only the exact electronic structure presented, but also include all resonance structures and protonation states thereof.)

FORMULA I

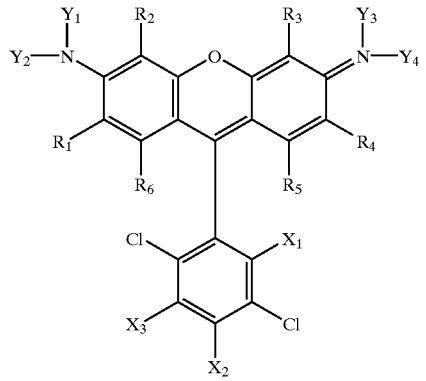

In Formula I, $R_1$ through $R_6$ are each hydrogen, fluorine, chlorine, lower alkyl, lower alkenyl, lower alkynyl, sulfonate, sulfone, amino, amido, nitrile, lower alkoxy, a linking group, or combinations thereof. Alternatively, when taken together $R_1$ and $R_6$ is benzo, and/or, $R_4$ and $R_5$ is benzo. In one specific embodiment, $R_1$ through 1% are each hydrogen, methyl, or ethyl. In another specific embodiment, $R_1$ through $R_6$ are each hydrogen or methyl.

$Y_1$ through $Y_4$ are each hydrogen or lower alkyl. Alternatively, $Y_1$ taken together with $R_2$ is propylene (—$CH_2$—$CH_2$—$CH_2$—), and $Y_2$ taken together with $R_1$ is propylene, and/or, $Y_3$ taken together with $R_3$ is propylene and $Y_4$ taken together with $R_4$ is propylene. In one specific embodiment, $Y_1$ through $Y_4$ are each hydrogen, methyl, or ethyl.

$X_1$–$X_3$ are each hydrogen, chlorine, fluorine, lower alkyl, carboxylate, sulfonic acid, —$CH_2OH$, or a linking group. In one embodiment, $X_1$ is carboxylate. In one specific embodiment, one of $X_2$ or $X_3$ is a linking group.

In one particularly compound suitable for use with the present invention, referred to herein as DR110, $R_1$–$R_6$ are each hydrogen, $Y_1$–$Y_4$ are each hydrogen, $X_1$ is carboxylate, and one of $X_2$ and $X_3$ is a linking group (L), the other being hydrogen. The structure of DR110 is shown below as Formula II.

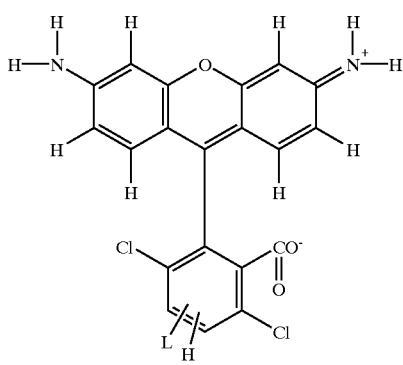

FORMULA II

A second particularly compound suitable for use with the present invention, referred to herein as DR6G, $R_1$ and $R_4$ are each methyl, $R_2$, $R_3$, $R_5$, and $R_6$ are hydrogen, one of $Y_1$ and $Y_2$ is ethyl, the other being hydrogen, one of $Y_3$ and $Y_4$ is ethyl, the other being hydrogen, $X_1$ is carboxylate, and one of $X_2$ and $X_3$ is a linking group, the other being hydrogen. The structure of DR6G is shown below as Formula III.

FORMULA III

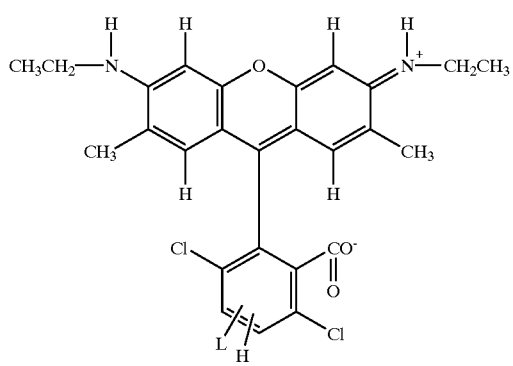

A third particularly compound suitable for use with the present invention, referred to herein as DTMR, $R_1$–$R_6$ are each hydrogen, $Y_1$–$Y_4$ are each methyl, $X_1$ is carboxylate, and one of $X_2$ and $X_3$ is a linking group, the other being hydrogen. The structure of DTMR is shown below as Formula IV.

FORMULA IV

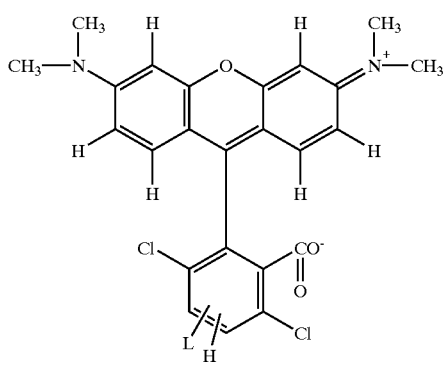

A fourth particularly compound suitable for use with the present invention, referred to herein as DROX, $R_1$ and $Y_2$ taken together are propylene, $R_2$ and $Y_1$ taken together are propylene, $R_3$ and $Y_3$ taken together are propylene, $R_4$ and $Y_4$ taken together are propylene, $R_5$ and $R_6$ are hydrogen, $X_1$ is carboxylate, and one of $X_2$ and $X_3$ is a linking group, the other being hydrogen. The structure of DROX is shown below as Formula V.

FORMULA V

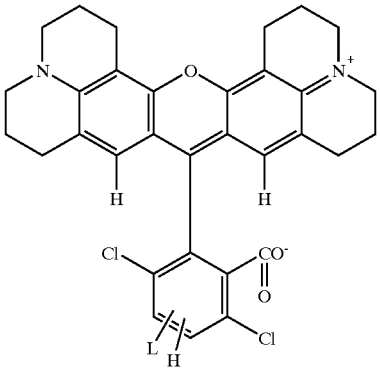

Several additional dye compounds suitable for use in the practice of the present invention are shown in FIGS. 6A–6F. In the compound having the structure shown in FIG. 6A, $R_1$ is methyl, $R_2$–$R_6$ are each hydrogen, one of $Y_1$ and $Y_2$ is ethyl, the other being hydrogen, $Y_3$ and $Y_4$ are each hydrogen, $X_1$ is carboxylate, and one of $X_2$ and $X_3$ is a linking group, the other being hydrogen. In the compound having the structure shown in FIG. 6B, $R_1$ is methyl, $R_2$–$R_6$ are each hydrogen, one of $Y_1$ and $Y_2$ is ethyl, the other being hydrogen, $Y_3$ and $Y_4$ are each methyl, $X_1$ is carboxylate, and, one of $X_2$ and $X_3$ is a linking group, the other being hydrogen. In the compound have the structure shown in FIG. 6C, $R_1$, $R_2$, $R_5$, and $R_6$ are each hydrogen, $Y_1$ and $Y_2$ are each methyl, $R_3$ and $Y_3$ taken together are propylene, $R_4$ and $Y_4$ taken together are propylene, $X_1$ is carboxylate, and, one of $X_2$ and $X_3$ is a linking group, the other being hydrogen. In the compound having the structure shown in FIG. 6D, $R_1$, $R_2$, $R_5$, and $R_6$ are each hydrogen, $Y_1$ and $Y_2$ are each hydrogen, $R_3$ and $Y_3$ taken together are propylene, $R_4$ and $Y_4$, taken together are propylene, $X_1$ is carboxylate, and one of $X_2$ and $X_3$ is a linking group, the other being hydrogen. In the compound having the structure shown in FIG. 6E, $R_1$ is methyl, $R_2$, $R_5$ and $R_6$ are each hydrogen, one of $Y_1$ and $Y_2$ is ethyl, the other being hydrogen, $R_3$ and $Y_3$ taken together are propylene, $R_4$ and $Y_4$ taken together are propylene, $X_1$ is carboxylate, and, one of $X_2$ and $X_3$ is a linking group, the other being hydrogen. In the compound having the structure shown in FIG. 6F, $R_1$–$R_6$ are each hydrogen, $Y_1$ and $Y_2$ are each hydrogen, $Y_3$ and $Y_4$ are each methyl, $X_1$ is carboxylate, and, one of $X_2$ and $X_3$ is a linking group, the other being hydrogen.

The introduction of fluorescein/d-rhodamine conjugated dyes, such as those shown in FIGS. 8A–8D and FIGS. 9A–9D, for use in the sequencing of nucleic acid sequencing products represent a major improvement in fluorescent detection. Fluorescein/d-rhodamine conjugated dyes have been compared to rhodamine and d-rhodamine dyes. The conjugated dyes were generally found to be brighter and to have a higher signal-to-noise ratio than their rhodamine and d-rhodamine counterparts. The structures and physical characteristics of the fluorescein/d-rhodamine conjugated dyes shown in FIGS. 8A–8D and FIGS. 9A–9D, as well as methods for their production, are disclosed in Rosenblum et al., *Nucleic Acids Res.* 25:4500–4504 (1997) and Lee et al., *Nucleic Acids Res.* 25:2816–2822 (1997).

The fluorescein/d-rhodamine conjugated dyes of Rosenblum et al. and Lee et al. consists of energy-transfer dyes which use the 5-carboxy-d-rhodamine dyes as acceptor dyes and 5- or 6-carboxy isomers of 4'-aminomethylfluorescein as donor dyes. Dyes of this type are sold by Perkin Elmer/ Applied Biosystems Incorporated under the trade name BigDyes™. See *ABI PRISM™ 377 DNA Sequencer User's Manual, Automated DNA Sequencing Chemistry Guide*, Part No. 4305080 (July 1998).

Methods for linking detectable labels to either nucleotides or primers are known in the art. When the fluorescent labels shown above are linked to a sequencing reaction reactant, these labels may be linked to either the sequencing primers or to nucleotides which become incorporated in the nucleic acid chain. The reagents shown in FIGS. 7A–7D and FIGS. 9A–9D, for examples, are linked to dideoxynucleotides which act as sequence reaction chain terminators. These reagents, as well as fluorescent dyes having the structures shown in FIGS. 6A–6F and FIGS. 8A–8D, are suitable for use in the practice of the present invention.

Generally, dyes such as those shown in FIGS. 6A–6F and FIGS. 8A–8D, are covalently attached to the reagent being labeled either directly or through a linkage. Exemplary reagents which can be labeled and used in the practice of the present invention include nucleotides, nucleosides, and polynucleotides.

One class of reagents suitable for use with the present invention comprise nucleotides and nucleosides which incorporate dyes having the structures shown in shown in FIGS. 6A–6F and FIGS. 8A–8D. Such nucleotide/side reagents are particularly useful in the context of labeling polynucleotides formed by enzymatic synthesis, e.g., nucleotide triphosphates used in the context of PCR amplification, Sanger-type polynucleotide sequencing, and nick-translation reactions.

Nucleotide/side reagents suitable for use with the present invention are shown below in Formula VI wherein

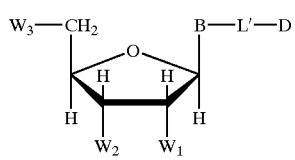

FORMULA VI

B is a nucleoside base, e.g., uracil, cytosine, deazaadenine, and deazaguanosine. $W_1$ and $W_2$ are each H, OH, or —$OCH_3$. $W_3$ is OH, —$PO_4$, —$P_2O_7$, —$P_3O_{10}$, or analogs thereof, e.g., phosphorothioate, phosphoroanilidate, phosphoroanilothioate, phosphoramidiate, and other like phosphate analogs, including associated counterions if present, e.g., H, Na, $NH_4$, and the like. D is a dye compound of Formula I; L' is a linkage linking B to D.

When B is purine or 7-deazapurine, the sugar moiety is attached at the $N^9$-position of the purine or deazapurine, and when B is pyrimidine, the sugar moiety is attached at the N'-position of the pyrimidine.

The linkage linking B and D may be attached to D at any one of positions $R_1$–$R_6$ or $X_1$–$X_3$. In one embodiment, the linkage is attached at one of $X_2$ or $X_3$. When B is a purine, the linkage linking B and D is generally attached to the 8-position of the purine, when B is 7-deazapurine, the linkage is attached to the 7-position of the 7-deazapurine, and when B is pyrimidine, the linkage is attached to the 5-position of the pyrimidine.

In one specific embodiment, nucleotides suitable for use in the practice of the present invention are dideoxynucleotide triphosphates having the structure shown below in Formula VII, including associated counterions if present.

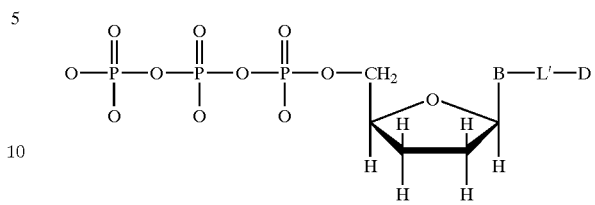

FORMULA VII

Labeled dideoxy nucleotides such as that shown in Formula VII find particular application as chain terminating agents, or "terminators", in Sanger-type DNA sequencing methods.

In a second specific embodiment, the nucleotides suitable for use with the present invention are deoxynucleotide triphosphates having the structure shown in Formula VIII below, including associated counterions if present.

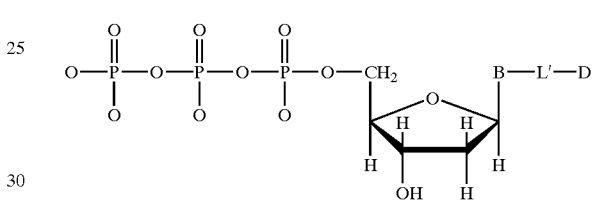

FORMULA VIII

Labeled deoxynucleotides such as that shown in Formula VIII find particular application as means for labeling polymerase extension products, e.g., in the polymerase chain reaction (Mullis, U.S. Pat. No. 4,683,202).

Nucleotide/side labeling can be accomplished using any of a large number of known nucleotide/side labeling techniques using known linking groups, and associated complementary functionalities to form linkages. The linkage linking the dye and nucleoside should (i) not interfere with oligonucleotide-target hybridization, (ii) be compatible with relevant enzymes, e.g., polymerases, ligases, and the like, and (iii) not quench the fluorescence of the dye.

In another embodiment, dyes suitable for use in the practice of the invention are covalently linked to the 5-carbon of pyrimidine bases or to the 7-carbon of 7-deazapurine bases. Several suitable base labeling procedures have been reported that can be used with the invention. (Gibson et al., *Nucleic Acids Research*, 15:6455–6467 (1987); Gebeyehu et al., *Nucleic Acids Research*, 15:4513–4535 (1987); Haralambidis et al., *Nucleic Acids Research*, 15:4856–4876 (1987), Nelson, *Nucleic Acids Research* 20:6253–6259 (1992a), Bergstrom et al., *JACS* 111:374–375 (1989); Fung et al., U.S. Pat. No. 4,757,141; Ward et al., U.S. Pat. No. 5,559,767; Woo et al., U.S. Pat. No. 5,231,191).

In another embodiment, the linkages are acetylenic amido or alkenic amido linkages, the linkage between the dye and the nucleotide base being formed by reacting an activated NHIS ester of the dye with an alkynylamino- or alkenylamino-derivatized base of a nucleotide. In a more specific embodiment, the resulting linkage is 3-(carboxy) amino-1-propynyl or 3-amino-1-propyn-1-yl (Formula IX.1). Several suitable linkages for linking the dyes to a nucleoside base are shown below as Formulas IX.1, IX.2, and IX.3.

FORMULA IX.1

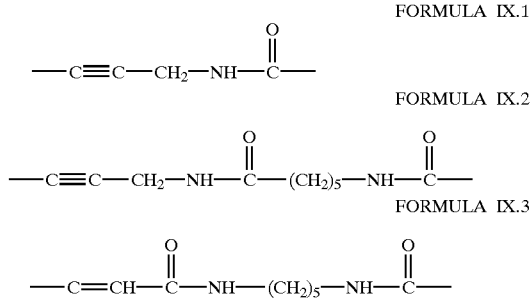

FORMULA IX.2

FORMULA IX.3

The synthesis of alkynylamino-derivatized nucleosides is described by (Hobbs et al., *J. Org. Chem.*, 54:3420 (1989); Hobbs et al., U.S. Pat. No. 5,151,507). Briefly, the alkynylamino-derivatized nucleotides are formed by placing the appropriate halodideoxynucleoside (usually 5-iodopyrimidine and 7-iodo-7-deazapurine dideoxynucleosides) and Cu(I) in a flask, flushing with argon to remove air, adding dry DMF, followed by addition of an alkynylamine, triethyl-amine and Pd(0). The reaction mixture is stirred for several hours, or until thin layer chromatography indicates consumption of the halodideoxynucleoside. When an unprotected alkynylamine is used, the alkynylamino-nucleoside can be isolated by concentrating the reaction mixture and chromatographing on silica gel using an eluting solvent which contains ammonium hydroxide to neutralize the hydro-halide generated in the coupling reaction. When a protected alkynylamine is used, methanol/ methylene chloride can be added to the reaction mixture, followed by the bicarbonate form of a strongly basic anion exchange resin. The slurry can then be stirred for about 45 minutes, filtered, and the resin rinsed with additional methanol/methylene chloride. The combined filtrates can be concentrated and purified by flash-chromatography on silica gel using a methanol-methylene chloride gradient. The triphosphates are obtained by standard techniques.

Yet another class of reagents suitable for use in the practice of the present invention comprise polynucleotides labeled with the dyes disclosed herein. Such labeled polynucleotides are useful in a number of important contexts including as DNA sequencing primers, PCR primers, oligonucleotide hybridization probes, and the like.

The polynucleotides suitable for use in the practice of the invention include a nucleotide having the formula:

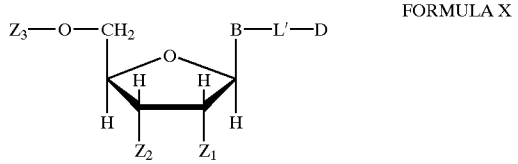

FORMULA X where B is a nucleotide base, e.g., 7-deazapurine, purine, or pyrimidine. $Z_1$ is H, OH or —OCH$_3$. $Z_2$ is OH, —PO$_4$, —P$_2$O$_7$, —P$_3$O$_{10}$, or analogs thereof, e.g., phosphorothioate, phosphoroanilidate, phosphoroanilothioate, phosphoramidiate, and other like phosphate analogs, including associated counterions if present, e.g., H, Na, NH$_4$, and the like, or Nuc, wherein Nuc refers to a nucleoside, nucleotide, or polynucleotide. The nucleotide of Formula X and Nuc are linked by a phosphodiester linkage or analog thereof, the linkage will generally being attached to the 5'-position of Nuc. $Z_3$ is H, —PO$_3$ or analogs thereof, or Nuc, wherein Nuc and the nucleoside are linked by a phosphodiester linkage or analog thereof attached to the 3'-position of Nuc. D is a dye compound of Formula I. Base B is attached to the sugar moiety and to the dye compound as described above for nucleotide reagents. As defined, the labeled nucleotide of Formula X can be the 5'-terminal nucleotide, the 3'-terminal nucleotide, or any internal nucleotide of the polynucleotide.

In one embodiment, the practice of the present invention includes the simultaneous use of multiple dyes for the detection of nucleic acid sequencing reaction products, including at least one of the dyes disclosed in FIGS. 6A–6F, FIGS. 7A–7D, FIGS. 8A–8D, and FIGS. 9A–9D. (See Ju et al., *Proc. Natl. Acad. Sci. USA* 92:4347–4351 (1995); Lee et al., *Nucleic Acids Research*, 21:3761–3766 (1993)).

Labeled polynucleotides may be synthesized either enzymatically, e.g., using a DNA polymerase or ligase (Stryer, *Biochemistry*, W. H. Freeman (1981)), or by chemical synthesis, e.g., by the phosphoramidite method, the phosphite-triester method, and the like (Gait, *Oligonucleotide Synthesis*, IRL Press (1990)). Labels may be introduced during enzymatic synthesis utilizing labeled nucleotide triphosphate monomers as described above or may be introduced subsequent to synthesis.

Generally, if the labeled polynucleotide is made by enzymatic synthesis, the following procedure may be used. A template DNA is denatured and an oligonucleotide primer is annealed to the template DNA. A mixture of deoxynucleotide triphosphates and/or dideoxynucleotide triphosphates is added to the reaction including dGTP, dATP, dCTP, ddTTP, ddGTP, ddATP, ddCTP, and ddTTP, where at least a fraction of one of at least one the deoxynucleotides and/or dideoxynucleotides is labeled with a dye compound as described above. Next, a polymerase enzyme is added under conditions where its polymerase activity is operative. A labeled polynucleotide is formed by the incorporation of the labeled deoxynucleotides and/or dideoxynucleotides during polymerase strand synthesis. In an alternative enzymatic synthesis method, two primers are used instead of one, one primer complementary to the +strand and the other complementary to the -strand of the target, the polymerase is a thermostable polymerase, and the reaction temperature is cycled between a denaturation temperature and an extension temperature, thereby exponentially synthesizing a labeled complement to the target sequence by PCR (Mullis, U.S. Pat. No. 4,683,202; Innis et al. eds., *PCR Protocols*, Academic Press (1990)).

Subsequent to synthesis, the polynucleotide may be labeled at a number of positions including the 5'-terminus (Eckstein ed., *Oligonucleotides and Analogs*, Chapters 8 and 9, IRL Press (1991); Orgel et al., *Nucleic Acids Research* 11:6513 (1983); Smith et al., *Nucleic Acids Res.*, 113:2399–2412 (1985)); the phosphodiester backbone (Eckstein ed., *Oligonucleotides and Analogs*, Chapters 8 and 9, IRL Press (1991)); or at the 3'-terminus (Nelson, *Nucleic Acids Res.* 20:6253–6259 (1992a); Nelson, U.S. Pat. No. 5,141,813; Nelson, U.S. Pat. No. 5,401,837. For a review of oligonucleotide labeling procedures see Steiner ed., *Excited States of Biopolymers*, Plenum Press (1983).

In one post-synthesis chemical labeling method an oligonucleotide is labeled as follows. A dye including a carboxylate linking group is converted to the NHS ester by reacting with approximately 1 equivalent of 1,3-dicyclohexylcarbodiimide and approximately 3 equivalents of N-hydroxysuccinimide in dry ethyl acetate for 3 hours at room temperature. The reaction mixture is washed with 5% HCl, dried over magnesium sulfate, filtered, and concentrated to a solid which is resuspended in DMSO. The DMSO dye stock is then added in excess (10–20 times) to an aminohexyl derivatized oligonucleotide in 0.25M bicarbonate/carbonate buffer at pH 9.4 and allowed to react for 6 hours (Fung et al., U.S. Pat. No. 4,757,141). The dye labeled oligonucleotide is separated from unreacted dye by passage through a size-exclusion chromatography column eluting with buffer, e.g., 0.1 molar triethylamine acetate (TEAA). The fraction containing the crude labeled oligonucleotide is further purified by reverse phase HPLC employing gradient elution.

As with the rhodamine and d-rhodamine dyes, fluorescein/d-rhodamine conjugated dyes can be further conjugated to either dideoxynucleotides or nucleic acid sequencing primers. Further, PE/ABI sells BigDye™ terminators and BigDye™ primers for use in sequencing reactions. See *ABI™ 377 DNA Sequencer User's Manual, Automated DNA Sequencing Chemistry Guide*, Part No. 4305080 (July 1998). PE/ABI further sells each of these BigDye™ products in kit for sequencing reactions. See *ABI PRISM BigDye™ Terminator Cycle Sequencing Ready Reaction Kit Protocol*, Part No. 4303237, Revision C. (September 1998) and *ABI PRISM BigDye™ Primer Cycle Sequencing Ready Reaction Kit Protocol*, Part No. 4303057, Revision C (1998). The use of fluorescein/d-rhodamine conjugated dyes, and in particular BigDyes™, to detect the sequencing products produced by the method of the present invention are within the scope of the invention.

Several groups have recently reporting the results of sequencing experiments performed with BigDyes™ Heiner et al., *Genome Res.* 8:557–561 (1998); Zakeri et al., *BioTechniques* 25:406–410414 (1998); Zakeri et al., *BioTechniques* 25:412–414 (1998); Salas-Solano et al., *Anal. Chem.* 70:3996–4003 (1998). These groups generally report that sequencing reactions performed with BigDyes™ result in long read lengths with low signal-to-noise ratios.

Subsequent to electrophoretic separation, dye-polynucleotide conjugates are generally detected by measuring the fluorescence emission from the dye labeled polynucleotides. To perform such detection, the labeled polynucleotides are illuminated by art known means, e.g., high intensity mercury vapor lamps or lasers). Argon ion lasers are available commercially which lase at lines which will excite fluorescent dyes (e.g., Models 2011, 2102, 2013, and 2014 from Uniphase Corp. (San Diego, Calif.)). Flourescent emissions are then detected by a light-sensitive detector (e.g., a photomultiplier tube or a charged coupled device).

B. Other Detection Methods

Another method for the detection of sequencing reaction products involves infrared fluorescence detection. One such detection method is disclosed in Steffens and Roy, *BioTechniques* 24:1044–1046 (1998). Iannelli et al., *Mol. Biotechnol.* 10:183–185 (1998) describe a method for the direct sequencing of PCR-generated templates using an automated infrared DNA sequencer which yields read lengths of 500–600 bases. European Patent Application EP 0 753 584 describes an automated methods for sequencing DNA labeled using far infrared, near infrared, and infrared fluorescent dyes.

Sequence reaction products can also be labeled with an appropriate radioisotope such as $p^{32}$, $H^3$, $S^{35}$ and $I^{131}$ and detected by autoradiography. Methods for detection of a radiolabeled sequencing reaction products are well known in the art (see Ausubel, F. M. et al., *Current Protocols in Molecular Biology*, John Wiley & Sons, Inc., New York, N.Y. (1993), Chapter 7).

As noted above, the methods of the present invention can be used for the high-throughput analysis of nucleic acid templates. In such instances, nucleotide sequences reaction will generally be performed using an automated DNA sequencer (such as the Model 373 from Applied Biosystems, Inc. and as described in Smith et al., U.S. Pat. No. 5,821,058).

Having generally described the invention, the same will be more readily understood by reference to the following examples, which are provided by way of illustration and are not intended as limiting.

EXAMPLES

Example 1

Direct Bacterial Lysate Sequencing (DBLS) in *E. coli*

To evaluate the performance of the DBLS method, we selected a large population of samples from multiple cDNA libraries and sequenced them using both DBLS and standard template sequencing methods. The success rate and average read length of the DBLS reactions were equal to or greater than the reactions performed with PCR and plasmid templates. The DBLS method was shown to work with all widely used reaction chemistries, a wide range of vectors, and most host cell strains.

Materials and Methods cDNA Library Construction cDNA libraries were constructed using the SuperScript Plasmid System for cDNA Synthesis and Plasmid Cloning (Catalog No. 18428-013, Life Technologies Inc., Rockville, Md.) or the ZAP-cDNA Synthesis System (Catalog No. 200450, Stratagene, LaJolla, Calif.) as outlined by the manufacturer. Total RNA was isolated using the TRIzol Reagent (Catalog No. 15596-026 Life Technologies Inc.) and mRNA isolated using Oligotex suspension (Catalog No. 79000, Qiagen, Valencia, Calif.) as outlined by the manufacturers.

Template Purification

Purification of either plasmid DNA or PCR products suitable for sequencing were performed using standards procedures (Ausubel, F. M. et al., *Current Protocols in Molecular Biology*, John Wiley & Sons, Inc., New York, N.Y. (1993)). High-throughput plasmid purification was performed using reagents purchased from 5' prime to 3' prime, Inc. PCR products were generated using the following profile: initial denaturation at about 95° C. for about 5 minutes followed by 30 cycles of about 20 seconds at about 95° C., about 20 seconds at about 55° C., about I minute at about 72° C. The amplified products were precipitated by the addition of PEG and NaCl as described (Ausubel, F. M. et al., *Current Protocols in Molecular Biology*, John Wiley & Sons, Inc., New York, N.Y. (1993)).

Direct Bacterinal Lysate Sequencing

Bacterial colonies were picked from agar plates using sterile toothpicks and used to inoculate 96-well plates containing 1 ml LB media per well. The plates were placed at about 37° C. and grown overnight with antibiotic selection and shaking. The bacteria were centrifuged at about 2135×g for about 10 minutes in the deep-well plates and the media was decanted. The bacterial pellets were resuspended in sterile deionized water, and centrifuged again. Following a second wash with water, the cells were resuspended in water and 50 µl transferred into 96 well PCR trays. The plates were placed at about 96° C. for about 20 minutes and the bacterial cells lysed. Subsequently the samples were cooled either on ice for about 5 minutes or at room temperature for about 5 minutes and then centrifuged at about 2135×g for about 10 minutes. The bacterial lysates were then used to perform cycle sequencing reactions as outlined by the manufacturer of the reaction chemistry.

Cycle Sequencing Reactions and Gel Analysis

Sequencing reactions were performed as outlined by the manufacturer of the reaction chemistries, either Applied Biosystems or Amersham. Briefly, either plasmid or PCR amplified template were used to set up cycle sequencing reactions as outlined by the manufacturer using the suggested method for GeneAmp 9600 PCR Systems. (See *ABI PRISM™ 377 DNA Sequencer User's Manual Automated DNA Sequencing Chemistry Guide*, Part No. 4305080 (July 1998).) The reactions were precipitated with ethanol and stored at −20° C. until loading. The samples were resuspended in formamide:EDTA and loaded onto ABI PRISM 377 with XL upgrade. Following gel electrophoresis the samples were processed using Sequencing Analysis 3.0 and average read lengths determined by both visual inspection and the ABI Factura feature identification software.

Results and Discussion

DBLS Method Development

In order to create a more efficient and cost effective sequencing process we investigated methods which would eliminate the need for substantial nucleic acid template purification prior to cycle sequencing. Previous efforts aimed at circumventing the template purification step have sacrificed sequencing data (Chen, Q. et al., *BioTechniques* 21:453–457 (1996); Wilson, R. et al., *BioTechniques* 8:184–189 (1990)). Using these first attempts as a foundation for our investigations, we developed the DBLS procedure. This method (FIG. 1) allows high quality sequencing data to be generated from bacterial lysates. Bacteria harboring plasmids containing genes of interest are plated on agar plates and grown overnight. The antibiotic resistant colonies are selected and used to inoculate liquid media. After overnight growth the cultures are centrifuged, the bacterial host cells are washed in sterile water and lysed by heating. Sequencing reactions are then performed on the cell lysates (FIG. 1 and Material and Methods). Some optimization of the procedure has been performed. The use of proteinase K and detergents, such as Triton X-100, showed no effect on the quality of the bacterial lysate sequencing (data not shown). Additionally, lysis times from 2–20 minutes at about 96° C. were tested with varying amounts of success, however a time of about 20 minutes at about 96° C. was chosen in order to insure complete bacterial lysis and plasmid denaturation without template degradation. Some samples, depending on tissue of origin, require an initial denaturation of 3–5 minutes at about 96° C. prior to entering the cycle sequencing profile. The effect of the bacterial host cell strain on the DBLS reaction is also minimal. We routinely achieve a reaction success rate over 75% with sample in many *E. coli* strains, including DH5alpha, DH10B, DH125, and XLI-Blue (data not shown). The DBLS method is not sensitive to different vectors, we routinely sequence a variety of cloning and expression vectors successfully.

Direct Bacterial lysate Sequencing

In order to evaluate the usefulness of the DBLS procedure as part of a large scale sequencing program, several thousand cDNA clones were sequenced using both DBLS and standard template preparation and sequencing methods. The clones were from both human and plant cDNA libraries and both plasmid and PCR products were used as template DNA. The sequencing data generated using the DBLS method was equal to or improved over standard methodologies with respect to reaction successate and average read length (Table 1).

DBLS reactions from the NTERA2 library had a higher-success percentage and longer average read length compared to sequencing reactions performed using purified plasmid as template. Similarly, the DBLS reactions of the colon library samples had a longer average read length and higher reaction success rate than the reactions set up with PCR amplified template DNA. The sequencing of the corn leaftissue library was comparable for all three sequencing methods, PCR, plasmid, and DBLS.

Due to interference of the recA protein with Taq polymerase, sequencing of templates from recA cell lines, such as DH125, is difficult. The sequencing of clones from cDNA libraries contained in a recA positive bacterial host is greatly improved using the DBLS method (Table 1). As shown by the results of the salivary gland library, sequencing by the DBLS method generated a significantly greater number of successful reactions. This probably is due to the destruction of the recA protein during lysis at about 96° C.

Comparison of Reaction Chemistries

Figure 2:
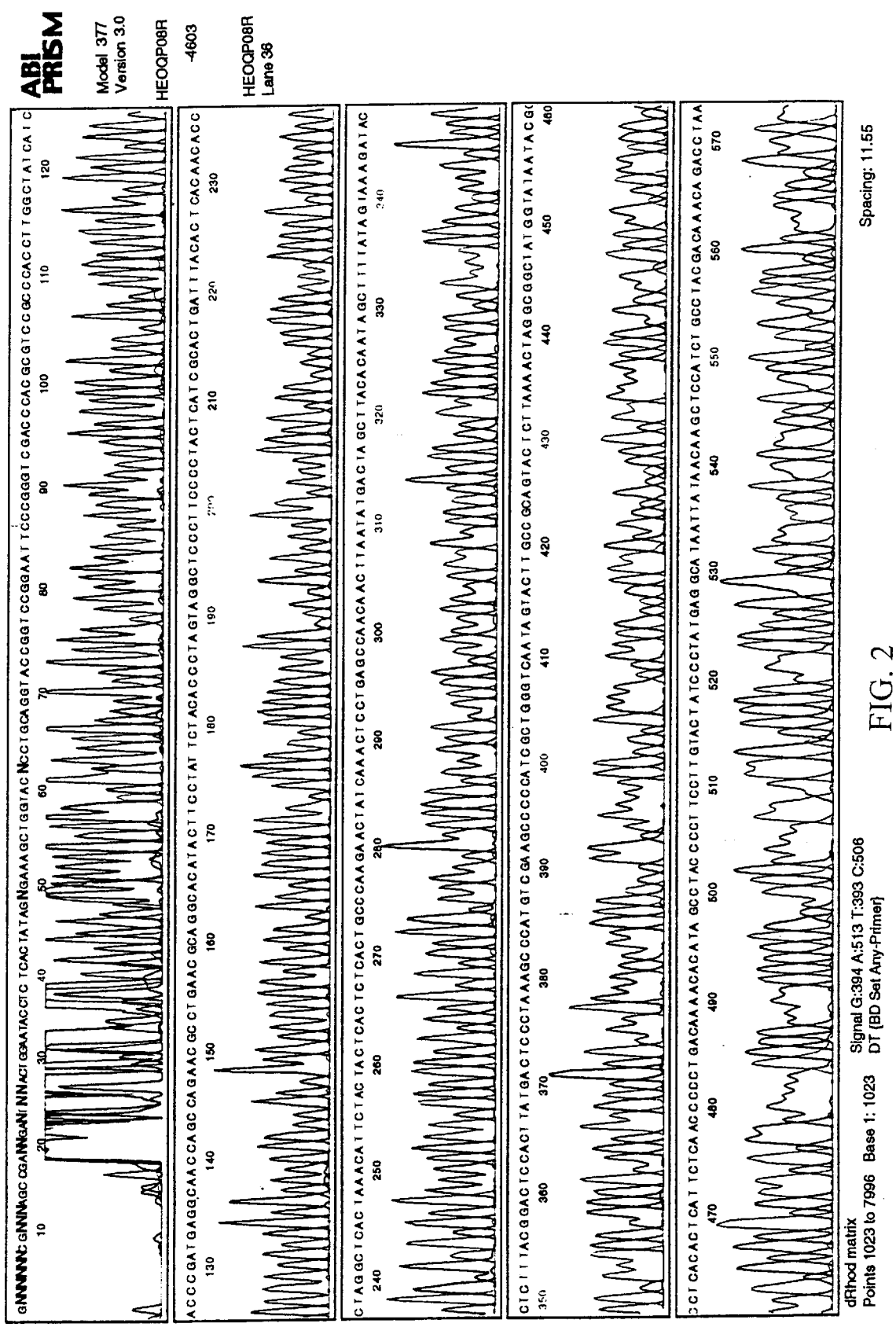
FIG. 2 shows an electropherogram obtained from DBLS. A human cDNA clone was reacted using DBLS, run on an ABI 377 with XL upgrade (ABI 377XL) for 10 hours, and the gel was analyzed using Sequencing Analysis 3.0. The electropherogram contains reliable base-calling information beyond 550 bases.

In order to identify the best reaction chemistry, the DBLS method was tested with several widely available reaction chemistries. Successful reactions were routinely obtained using Applied Biosystem Inc.'s BigDye™ dye terminator (FIG. 2) chemistry. Preliminary results with both Applied Biosystem Inc.'s BigDye™ dye primer and Amersham's Energy Transfer dye primer chemistry have been successful (data not shown). DBLS reactions performed with chemistries that do not use the energy transfer dye technology are rarely successful and usually have read lengths under 200 bases (data not shown). The majority of our DBLS samples are sequenced using 0.5×BigDye™ Terminator reactions.

Difficult Template Sequencing

Because of the high success rate of the DBLS reactions, we have utilized the method to sequence not only human and plant cDNA clones, but also human, mouse, and bacterial genomic DNA. A number of difficult templates, including GC-rich regions, long polyA tails, low complexity genomic sequence, and dinucleotide repeats (FIGS. 3–5) may seq. Future experiments will focus on using DBLS to rapidly sequence large insert genomic clones, such as BACs.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

TABLE 1

Comparison of Standard Sequencing Methods with DBLS Procedure

| Library | Species | Vector | Host Strain | Preparation Method | Total Reactions | Successful Reactions | Percent Success | Average Read Length |
|---|---|---|---|---|---|---|---|---|
| NTERA2 cells | Human | pCMV-SPORT3 | DH10B | Plasmid | 1955 | 1405 | 72 | 260 bases |
|  |  |  |  | DBLS | 1332 | 1091 | 82 | 310 |
| Colon | Human | pSPORT1 | DH10B | PCR | 348 | 261 | 75 | 268 |
|  |  |  |  | DBLS | 380 | 323 | 85 | 287 |

TABLE 1-continued

Comparison of Standard Sequencing Methods with DBLS Procedure

| Library | Species | Vector | Host Strain | Preparation Method | Total Reactions | Successful Reactions | Percent Success | Average Read Length |
|---|---|---|---|---|---|---|---|---|
| Salivary Gland | Human | pSPORT1 | DH12S | Plasmid | 672 | 410 | 61 | 274 |
| | | | | DBLS | 760 | 618 | 81 | 257 |
| Leaf Tissue | Corn | pSPORT1 | DH10B | Plasmid | 570 | 368 | 65 | 266 |
| | | | | PCR | 570 | 443 | 78 | 317 |
| | | | | DBLS | 665 | 447 | 67 | 242 |

Comparison of Standard Sequencing Methods with DBLS Procedure. The table outlines the results of sequencing several different cDNA libraries. By performing the sequencing reactions using the bacterial lyrate as template the quality of the data was comparable (colon and leaf tissue libraries) or improved (salivary gland and NTERA2 libraries) versus the normal methods.

What is claimed is:

1. A method for sequencing a nucleic acid template comprising:
    (a) incubating bacterial host cells containing the nucleic acid template at about 95° C. to about 96° C. for about 20 to about 25 minutes to produce a cell lysate; and
    (b) sequencing the nucleic acid template in the cell lysate using a sequencing reaction and one or more detectable labels to detect the products of the sequencing reaction, wherein the nucleic acid template is not purified from highly soluble cellular components released from the bacterial host cells upon lysis and is not amplified by polymerase chain reaction.

2. The method of claim 1 comprising washing the bacterial host cell with water prior to lysing.

3. The method of claim 2 comprising lysing the bacterial host cell in water.

4. The method of claim 1 wherein the cell lysate is incubated between about 4 and about 15° C. prior to sequencing.

5. The method of claim 4 wherein the cell lysate is centrifuged prior to sequencing.

6. The method of claim 5 wherein the cell lysate is incubated for about 5 minutes prior to centrifugation.

7. The method of claim 6 wherein the bacterial host cell is *Escherichia coli*.

8. The method of claim 7 comprising culturing the bacterial host cell in a broth selected from the group consisting of:
    (a) Luria broth; and
    (b) Terrific broth,
prior to lysing.

9. The method of claim 1 wherein the detectable labels comprise one or more fluorescent dyes.

Figure 6A:
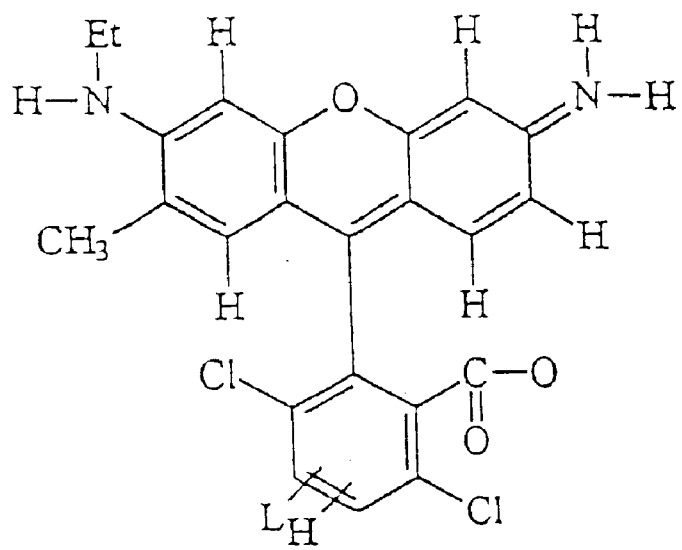
FIGS. 6A–6F show a series of fluorescent high intensity dyes which are suitable for use in detecting the sequence reaction products produced according to the present invention. These dyes are disclosed in Lee et al., U.S. Pat. No. 5,847,162 and PCT publication WO 97/49769.
Figure 6B:
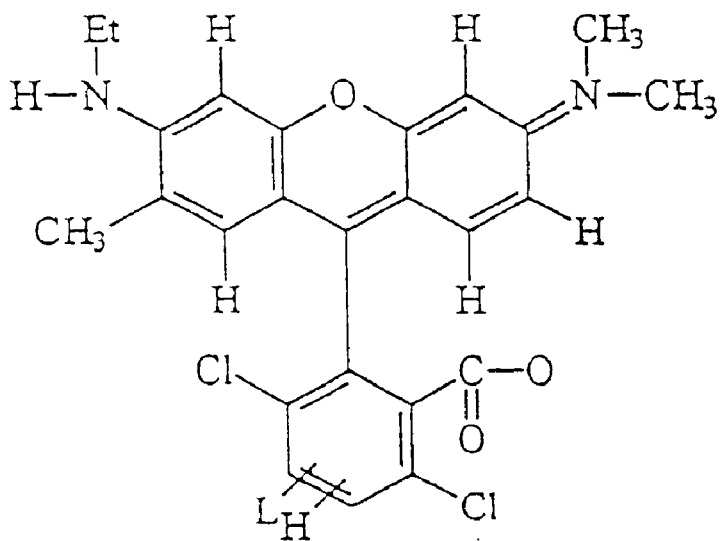
Figure 6C:
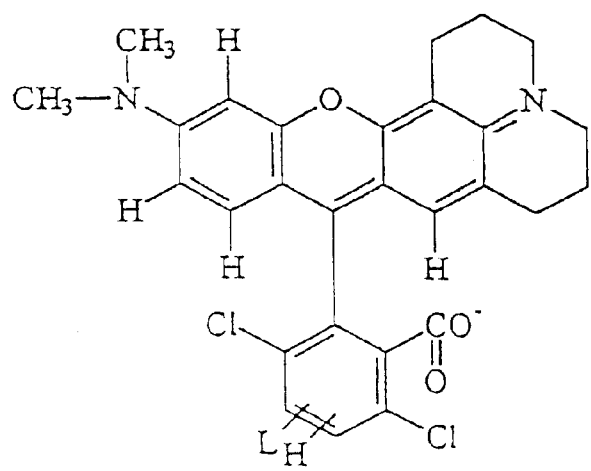
Figure 6D:
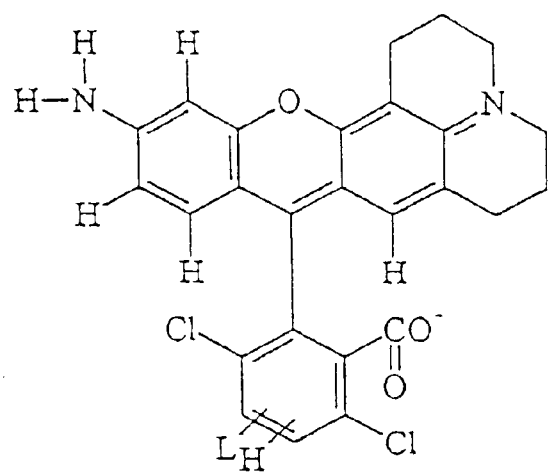
Figure 6E:
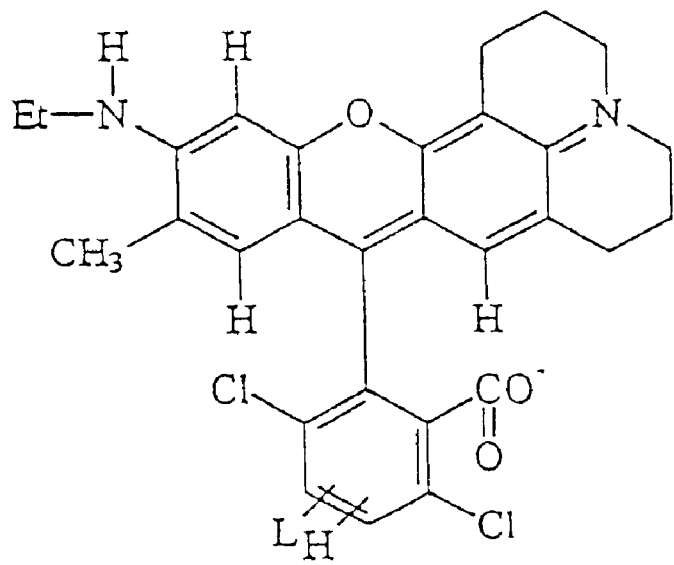
Figure 6F:
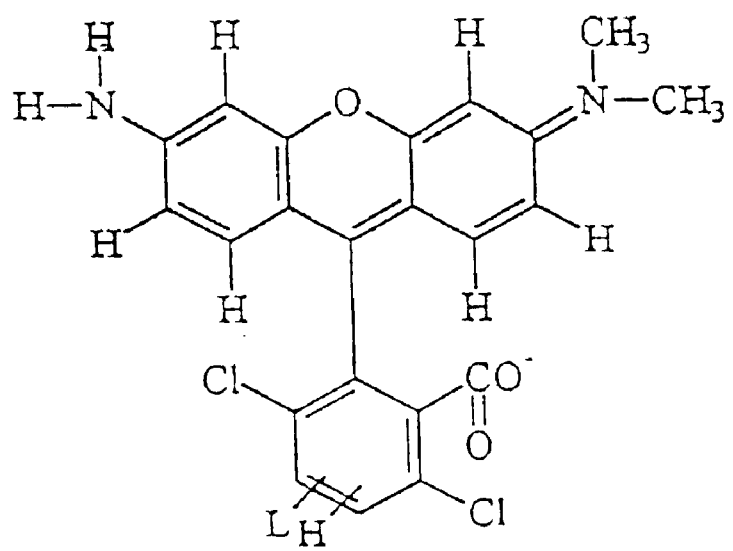

10. The method of claim 9 wherein the fluorescent dyes are d-rhodamine dyes having structural formulas shown in (FIG. 6A), (FIG. 6B), (FIG. 6C), (FIG. 6D), (FIG. 6E) or (FIG. 6F).

Figure 7A:
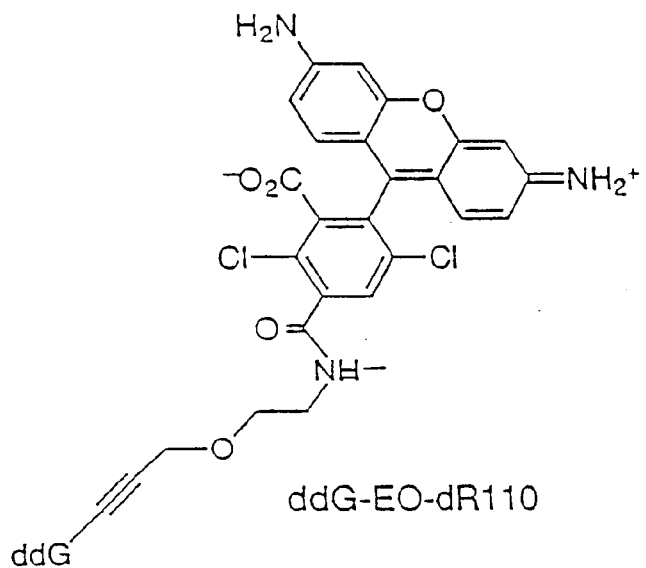
FIGS. 7A–7D show a series of d-rhodamine fluorescent dyes linked to various dideoxynucleotides. These dyes, would primarily be used as labeled chain terminators, are also suitable for use in detecting the sequence reaction products produced as part of the practice of the present invention. The dye complexes shown in FIGS. 7A–7D are disclosed in *ABI PRISM™ 377 DNA Sequencer User's Manual, Automated DNA Sequencing Chemistry Guide*, Part No. 4305080 (July 1998).
Figure 7B:
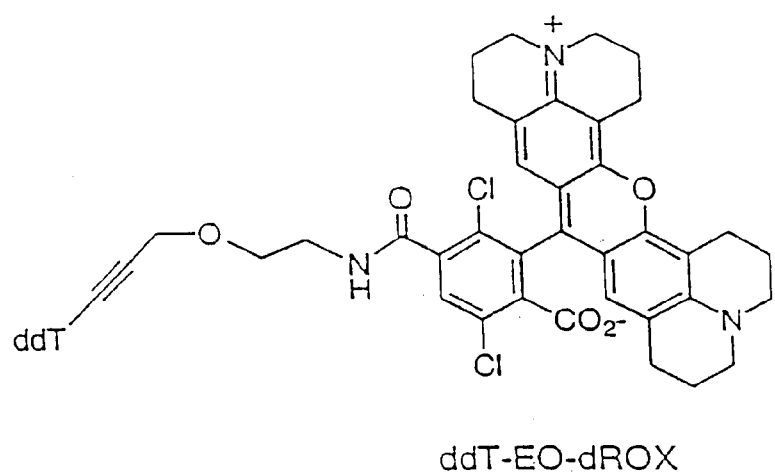
Figure 7C:
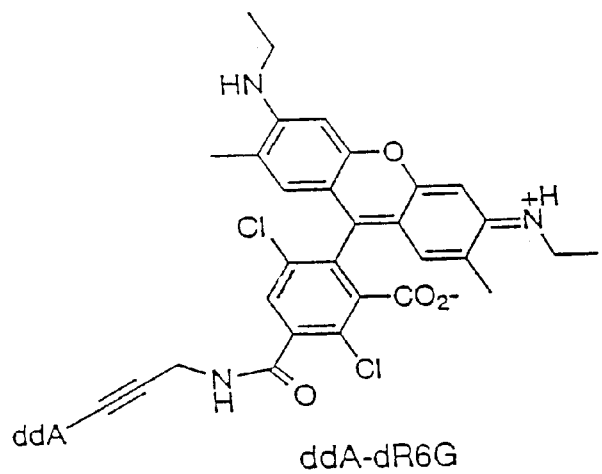
Figure 7D:
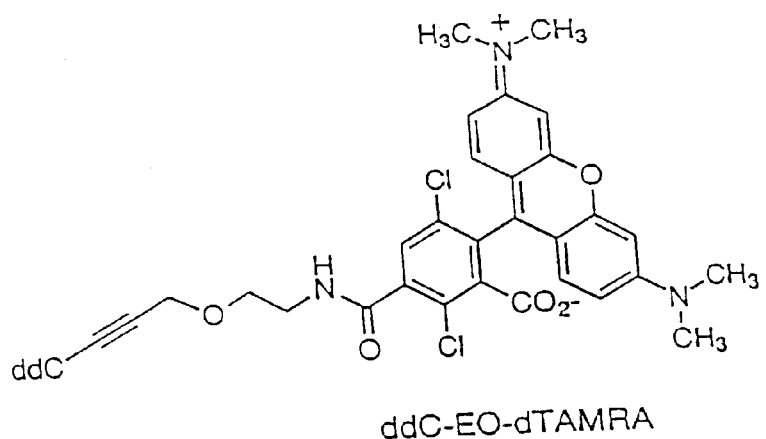

11. The method of claim 9 wherein the fluorescent dyes are d-rhodamine dyes having structural formulas shown in (FIG. 7A), (FIG. 7B), (FIG. 7C) or (FIG. 7D).

Figure 8A:
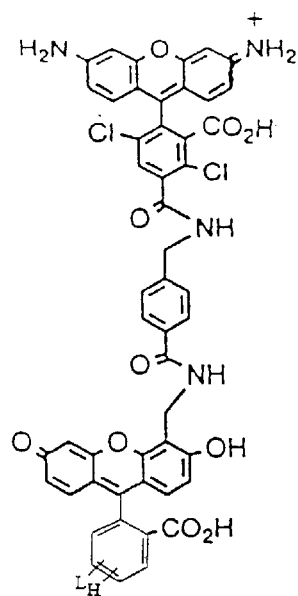
FIGS. 8A–8D show a series of fluorescein/d-rhodamine fluorescent dyes. These dyes are suitable for use in detecting the sequence reaction products produced according to the present invention and could be linked to either dideoxynucleotides, for use as chain terminators, or linked to primers. Dye complexes having similar structures are disclosed in Rosenblum et al., *Nucleic Acids Res.* 25:4500–4504(1997) and Lee et al., *Nucleic Acids Res.* 25:2816–2822 (1997) and described in *ABI PRISM™ 377 DNA Sequencer User's Manual, Automated DNA Sequencing Chemistry Guide*, Part No. 4305080 (July 1998).
Figure 8B:
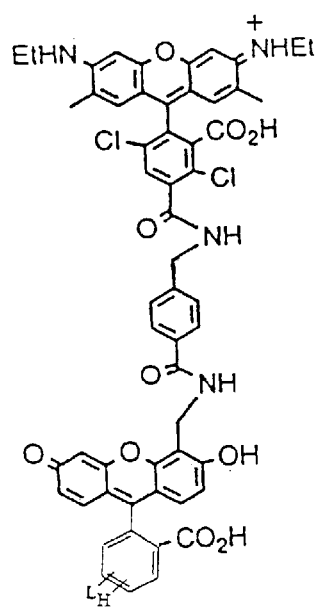
Figure 8C:
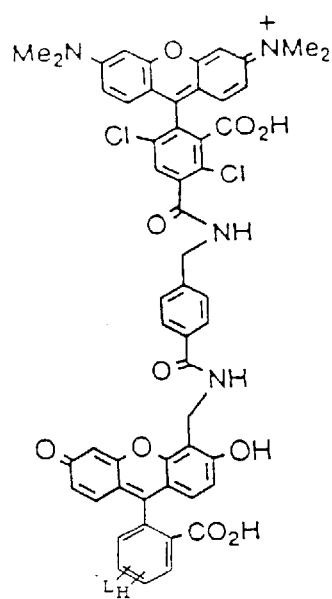
Figure 8D:
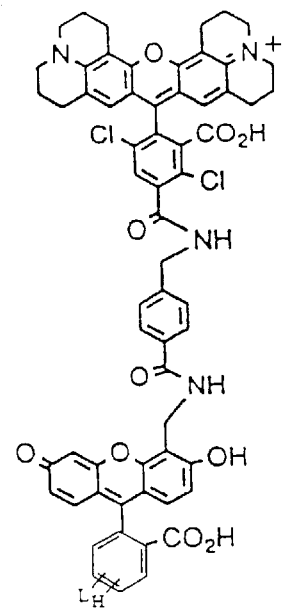

12. The method of claim 9 wherein the fluorescent dyes are fluorescein/d-rhodamine dyes having structural formulas shown in (FIG. 8A), (FIG. 8B), (FIG. 8C) or (FIG. 8D).

Figure 9A:
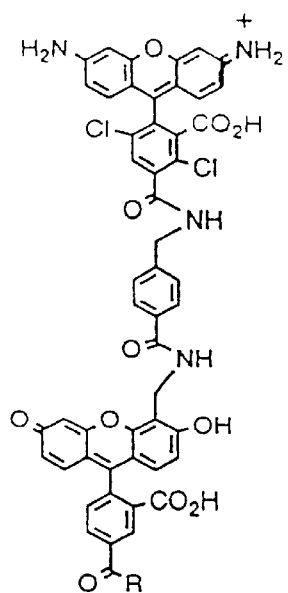
FIGS. 9A–9D show the chemical structures of a set of fluorescent/d-rhodamine conjugate dyes disclosed in Rosenblum et al., *Nucleic Acids Revs.* 25:4500–4504 (1997) and Lee et al., *Nucleic Acid. Res.* 25:2816–2822 (1997). Dyes of this nature are also described in *ABI PRISM™ 377 DNA Sequencer User's Manual, Automated DNA Sequencing Chemistry Guide*, Part No. 4305080 (July 1998). These dyes, which would primarily be used as labeled chain terminators, are suitable for use in detecting the sequence reaction products produced according to the present invention. Dyes of this type are sold by Perkin Elmer/Applied Biosystems Incorporated (PE/ABI) under the trade name "BigDyes™".
Figure 9B:
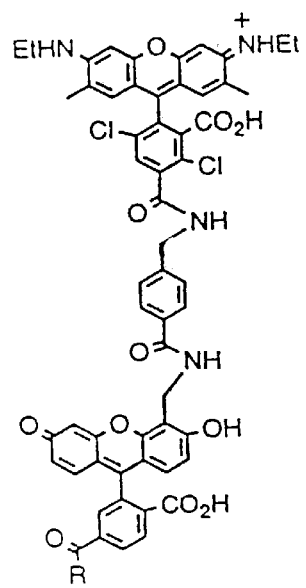
Figure 9C:
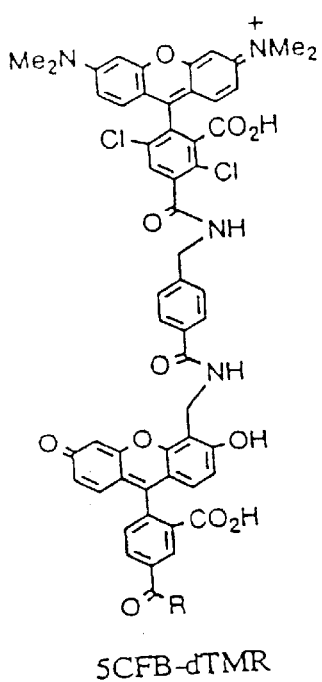
Figure 9D:
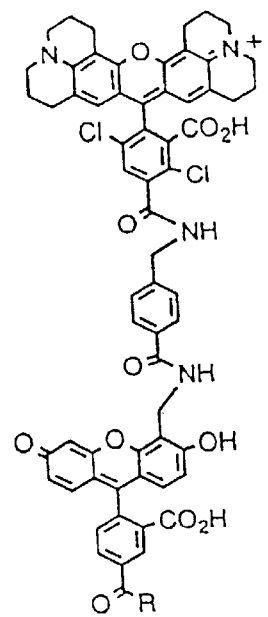

13. The method of claim 12 wherein the fluorescent dyes are fluorescein/d-rhodamine dyes having structural formulas shown in (FIG. 9A), (FIG. 9B), (FIG. 9C) or (FIG. 9D).

14. The method of claim 1 wherein the detectable labels comprise infrared labels.

15. A method for sequencing a nucleic acid template comprising:
    (a) incubating bacterial host cells containing the nucleic acid template at about 95° C. to about 96° C. for about 20 to about 25 minutes to produce a cell lysate; and
    (b) forming in the cell lysate a mixture of a first, a second, a third, and a fourth class of polynucleotides such that:
        (i) the polynucleotides in the first class include a 3'-terminal dideoxyadenosine and are labeled with a first detectable label;
        (ii) the polynucleotides in the second class include a 3'-terminal dideoxycytidine and are labeled with a second detectable label;
        (iii) the polynucleotides in the third class include a 3'-terminal dideoxyguanosine and are labeled with a third detectable label;
        (iv) the polynucleotides in the fourth class include a 3'-terminal dideoxythymidine and are labeled with a fourth detectable label;
wherein the nucleic acid template is not purified from highly soluble cellular components released from the bacterial host cells upon lysis and is not amplified by polymerase chain reaction.

16. The method of claim 15 wherein the detectable labels comprise one or more fluorescent dyes.

17. The method of claim 16 wherein the fluorescent dyes are d-rhodamine dyes having structural formulas shown in (FIG. 6A), (FIG. 6B), (FIG. 6C), (FIG. 6D), (FIG. 6E) or (FIG. 6F).

18. The method of claim 16 wherein the fluorescent dyes are d-rhodamine dyes having structural formulas shown in (FIG. 7A), (FIG. 7B), (FIG. 7C) or (FIG. 7D).

19. A method of sequencing a nucleic acid template comprising:
    (a) hybridizing a primer to the nucleic acid template;
    (b) forming a mixture comprising the nucleic acid template, deoxyadenosine triphosphate, deoxycytidine triphosphate, deoxyguanosine triphosphate, and deoxythymidine triphosphate, a DNA polymerase, and a dideocynucleotide;
    (c) incubating the mixture of (b) under conditions sufficient to synthesize a population of DNA molecules complementary to a portion of the nucleic acid template; and
    (d) separating said synthesized DNA molecules by size so that at least a part of the nucleotide sequence of the nucleic acid template can be determined; wherein:
        (a) the nucleic acid template is present in a cell lysate prepared by incubating bacterial host cells which contain the nucleic acid template at about 95° C. to about 96° C. for about 20 to about 25 minutes;
        (b) the nucleic acid template is not purified from highly soluble cellular components released from the bacterial host cells upon lysis and is not amplidied by polymerase chain reaction; and (c) the members of the population of DNA molecules are labeled with a detectable label.

20. The method of claim 19 wherein the detectable label comprises one or more fluorescent dyes.

21. The method of claim 20 wherein the fluorescent dyes are d-rhodamine dyes having structural formulas shown in (FIG. 6A), (FIG. 6B), (FIG. 6C), (FIG. 6D), (FIG. 6E) or (FIG. 6F).

22. The method of claim 20 wherein the fluorescent dyes are d-rhodamine dyes having structural formulas shown in (FIG. 7A), (FIG. 7B), (FIG. 7C) or (FIG. 7D).

23. The method of claim 20 wherein the fluorescent dyes are fluorescein/d-rhodamine dyes having structural formulas shown in (FIG. 8A), (FIG. 8B), (FIG. 8C) or (FIG. 8D).

24. The method of claim 23 wherein the fluorescent dyes are fluorescein/d-rhodamine dyes having structural formulas shown in (FIG. 9A), (FIG. 9B), (FIG. 9C) or (FIG. 9D).

25. The method of claim 19 wherein the detectable labels comprise one or more infrared labels.

26. A method for high-throughput sequencing of nucleic acid templates comprising:

(a) culturing more than one bacterial host cell such that host cells containing the same nucleic acid templates are separated from host cells containing different nucleic acid templates;

(b) lysing the cells of at least one bacterial host cell by incubating said cells at about 95° C. to about 96° C. for about 20 to about 25 minutes to produce a cell lysate; and (c) sequencing the nucleic acid template in the cell lysate using a sequencing reaction and one or more detectable labels to detect the products of the sequencing reaction, wherein:

(a) the detectable labels comprise fluorescent dyes;

(b) the nucleic acid template is not purified from highly soluble cellular components released from the bacterial host cells upon lysis; and (c) the nucleic acid template is not amplified by polymerase chain reaction.

27. The method of claim 26 wherein the fluorescent dyes are d-rhodamine dyes having structural formulas shown in (FIG. 6A), (FIG. 6B), (FIG. 6C), (FIG. 6D), (FIG. 6E) or (FIG. 6F).

28. The method of claim 26 wherein the fluorescent dyes are d-rhodamine dyes having structural formulas shown in (FIG. 7A), (FIG. 7B), (FIG. 7C) or (FIG. 7D).

29. The method of claim 26 wherein the fluorescent dyes are fluorescein/d-rhodamine dyes having structural formulas shown in (FIG. 8A), (FIG. 8B), (FIG. 8C) or (FIG. 8D).

30. The method of claim 29 wherein the fluorescent dyes are fluorescein/d-rhodamine dyes having structural formulas shown in (FIG. 9A), (FIG. 9B), (FIG. 9C) or (FIG. 9D).

31. The method of claim 26 comprising culturing more than one bacterial host cell on a solid culture medium to produce colonies.

32. The method of claim 31 comprising the transfer of cells of the colonies to a liquid culture medium for culturing.

* * * * *